(12) United States Patent
Pusey

(10) Patent No.: US 8,981,318 B1
(45) Date of Patent: Mar. 17, 2015

(54) MULTI-DIMENSIONAL SCANNER FOR NANO-SECOND TIME SCALE SIGNAL DETECTION

(71) Applicant: Marc L. Pusey, Huntsville, AL (US)

(72) Inventor: Marc L. Pusey, Huntsville, AL (US)

(73) Assignee: Gene Capture, Inc., Huntsville, AL (US)

( * ) Notice: Subject to any disclaimer, the term of this patent is extended or adjusted under 35 U.S.C. 154(b) by 222 days.

(21) Appl. No.: 13/731,097

(22) Filed: Dec. 30, 2012

Related U.S. Application Data

(60) Provisional application No. 61/582,172, filed on Dec. 30, 2011.

(51) Int. Cl.
*G01T 1/10* (2006.01)
*G21H 3/02* (2006.01)
*G01N 21/64* (2006.01)

(52) U.S. Cl.
CPC .................. *G01N 21/6408* (2013.01)
USPC .................... 250/458.1; 250/459.1

(58) Field of Classification Search
CPC .......... G01N 21/6428; G01N 21/6458; G01N 21/6408
USPC .......................... 250/458.1, 459.1
See application file for complete search history.

(56) References Cited

U.S. PATENT DOCUMENTS

| | | | |
|---|---|---|---|
| 4,368,047 A | 1/1983 | Andrade et al. | |
| 4,626,684 A | 12/1986 | Landa | |
| 5,237,101 A | 8/1993 | Nicolaou et al. | |
| 5,419,966 A | 5/1995 | Reed et al. | |
| 5,446,137 A | 8/1995 | Maag et al. | |
| 5,494,793 A | 2/1996 | Schindele et al. | |
| 5,512,667 A | 4/1996 | Reed et al. | |
| 5,574,142 A | 11/1996 | Meyer et al. | |
| 5,585,639 A | 12/1996 | Dorsel | |
| 5,714,331 A | 2/1998 | Buchardt et al. | |
| 5,801,155 A | 9/1998 | Kutyavin et al. | |
| 5,880,287 A | 3/1999 | Dandliker et al. | |
| 6,072,046 A | 6/2000 | Reed et al. | |
| 6,200,752 B1 | 3/2001 | Lakowicz | |
| 6,472,153 B1 | 10/2002 | Dempcy et al. | |
| 6,596,499 B2 | 7/2003 | Jalink | |
| 6,741,344 B1 | 5/2004 | Stern | |
| 6,951,930 B2 | 10/2005 | Dempcy et al. | |
| 7,291,459 B2 | 11/2007 | Pusey et al. | |
| 7,348,141 B2 | 3/2008 | French et al. | |
| 7,399,591 B2 | 7/2008 | Bao et al. | |
| 7,429,655 B2 | 9/2008 | Kurane et al. | |
| 7,670,832 B2 | 3/2010 | Wittwer et al. | |

(Continued)

OTHER PUBLICATIONS

K. Yamasaki et al., An Inexpensive handmade gated generator, Rev., Sci. Instrum., 66 (1996) 4395-4396.

*Primary Examiner* — David Porta
*Assistant Examiner* — Mindy Vu
(74) *Attorney, Agent, or Firm* — Sci-Law Strategies, PC

(57) ABSTRACT

A device and system for measuring the multidimensional distribution of a sample tagged with a short life fluorescent label. The substance applied to a sample holder can be scanned with an optical point source excitation and read back optical stage. The sample can be excited at each of a plurality of points with a fast, e.g., nanosecond pulse of light. The resulting fluorescence can be detected after the excitation is extinguished. A detection gate window can be optimized to maximize the fluorescence signal detected for a predetermined amount of time.

19 Claims, 9 Drawing Sheets

(56) References Cited

U.S. PATENT DOCUMENTS

| | | |
|---|---|---|
| 7,738,086 B2 * | 6/2010 | Shepard et al. ................ 356/73 |
| 7,767,435 B2 | 8/2010 | Chiu et al. |
| 7,785,795 B2 | 8/2010 | Kurata et al. |
| 7,790,406 B2 | 9/2010 | Cunningham et al. |
| 7,981,868 B2 | 7/2011 | Monia et al. |
| 8,138,301 B2 | 3/2012 | Newkome et al. |
| 8,629,830 B2 * | 1/2014 | Barnhoefer et al. .......... 345/102 |
| 2004/0036838 A1 * | 2/2004 | Podoleanu et al. ........... 351/206 |
| 2006/0134644 A1 * | 6/2006 | Hartel et al. ...................... 435/6 |
| 2007/0190537 A1 | 8/2007 | Park et al. |
| 2007/0197894 A1 | 8/2007 | Jo et al. |
| 2008/0064070 A1 | 3/2008 | Park et al. |
| 2008/0265177 A1 * | 10/2008 | Connally et al. ........... 250/461.2 |

* cited by examiner

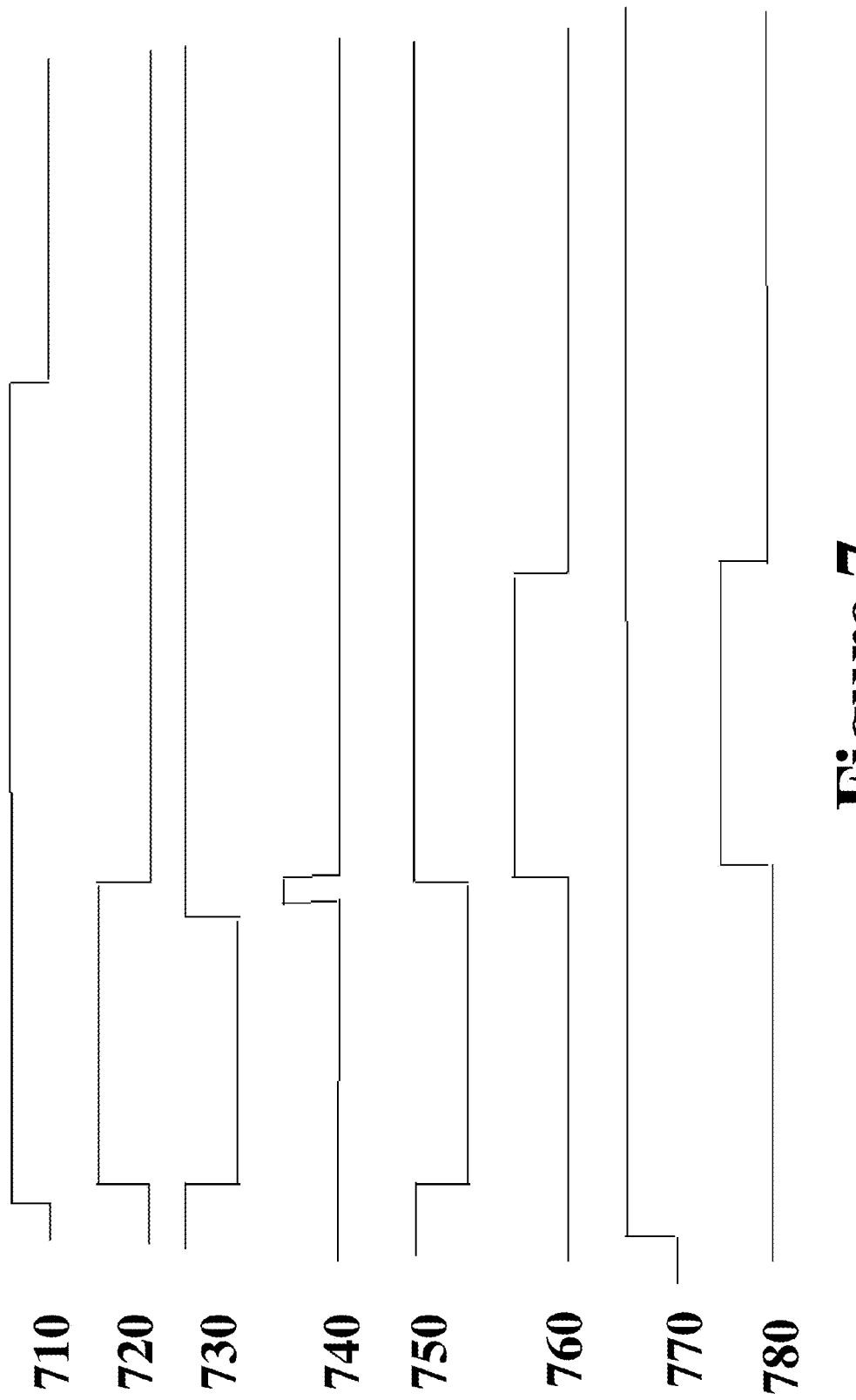

US 8,981,318 B1

MULTI-DIMENSIONAL SCANNER FOR NANO-SECOND TIME SCALE SIGNAL DETECTION

PRIORITY CLAIM

This application claims priority to U.S. provisional application 61/582,172 titled Multi-Dimensional Scanner For Nano-Second Time Scale Signal Detection, filed Dec. 30, 2011, inventor Marc Pusey, which is expressly incorporated by reference in its entirety.

FIELD OF THE INVENTION

The present invention pertains generally to the field of detection of nano-second time scale signal detection.

BACKGROUND OF THE INVENTION

Fluorescence is a process in which a molecule having suitable properties absorbs a photon of a given wavelength (the excitation process), resulting in the molecule in the excited state being raised to a higher energy level. The molecule referred to as a fluorophore can then drop down to a lower energy state by releasing a photon at a higher wavelength (lower energy), in the emission process. This energy can also be lost as heat to the surrounding environment, without the emission of a photon. The ratio of photons absorbed to emitted is known as the quantum efficiency. The difference between the excitation and emission spectral peak wavelengths is known as the Stokes shift.

The average time a fluorophore stays in the excited state prior to photon emission is known as its lifetime. This is an exponential decay process, following a rate defined by $e^{-\Gamma t}$, where $\Gamma$ is the decay rate which is the inverse of the fluorescence lifetime and t is the time. Fluorescent probes are commercially available having a wide range of lifetimes, from less than 1 ns to well over 1 microsecond. All properties of a fluorescent probe are taken into consideration when making a choice for a particular application. Probes having longer lifetimes typically have lower quantum yields.

Another factor in the performance of fluorescent probes is their absorptivity, or ability to 'capture' photons. Probes having a high absorptivity and a high quantum yield can be considered as high performance. For a given photon flux rate molecules that absorb more photons will have more to emit, independent of quantum yield.

Covalent attachment of a fluorophore to an oligonucleotide primer can be used to label a DNA fragment. When different colored fluorophores are used for the bases A, C, G and T, then the fluorescence can be used to sequence DNA. Protein microarrays can be used to identify a myriad of biological players including protein-protein interactions, the ligands for receptors or binding proteins, the substrates of protein kinases, or the proteins that activate transcription factors. The array can be a substrate upon which capture probes have been affixed at separate locations with appropriate fluorophores in an ordered manner. Fluorescent detection is compatible with standard microarray scanners, the spots on the resulting image can be quantified by commonly used microarray quantification software packages.

Fluorescent proteins are commonly used in order to undertake live cell imaging. The fluorescent proteins can be highly specific bio sensors used to monitor a wide range of intracellular phenomena, including pH, metal-ion concentration, protein kinase activity, apoptosis, membrane voltage, cyclic nucleotide signaling, and tracing neuronal pathways. Flow cytometry can be used to count and examine cells by suspending them in a stream of fluid and passing them by fluorescence detection system. A wide range of fluorophores can be used as labels in flow cytometry. Fluorophores can be conjugated to a protein that recognizes a target feature on or in the cell. Different fluorophores with characteristic excitation and emission wavelengths can be used to label different features. In some cases, the emission wavelengths can overlap with the excitation wavelength of the same or another fluorophore.

SUMMARY OF THE INVENTION

In an embodiment of the present invention very short decay time fluorescence can be detected using a high speed switching circuit to selectively direct the desired component of a repetitive signal to the detection mechanism. In an embodiment of the present invention very short decay time fluorescence can be detected using a Field Effect Transistor (FET) switch to selectively direct the desired component of a repetitive signal to the detection mechanism. Under these conditions, it is important that the photo multiplier tube (PMT) is highly responsive to the input light, particularly when the light is turned off. The data collection process is repeated a number of times depending on integration capacitor, with a pulse sent to an electronic switch at the end of the light pulse. In an embodiment of the present invention, the data collection process is repeated ten times with a pulse sent to an electronic switch at the end of the light pulse. In an alternative embodiment of the present invention, the data collection process is repeated one hundred times with a pulse sent to an electronic switch at the end of the light pulse. The switch integrated circuit (IC) connects the signal path from the PMT to the data input component of the circuit. In an embodiment of the present invention, a 74CBT1G12, FET Bus Switch, which has a switching speed of less than five (5) nano seconds (ns) and an 'on' resistance of five (5) ohms can be used.

BRIEF DESCRIPTION OF THE DRAWINGS

This invention is described with respect to specific embodiments thereof. The present invention is described with reference to the accompanying drawings. In the drawings, like reference numbers indicate identical or functionally similar elements. Additionally, the left-most digit(s) of a reference number identifies the drawing in which the reference number first appears. Additional features can be appreciated from the Figures in which:

FIG. 7 shows a schematic diagram of the output excitation light pulse width according to various embodiments of the invention.

DETAILED DESCRIPTION OF THE INVENTION

Definitions

Figure 1:
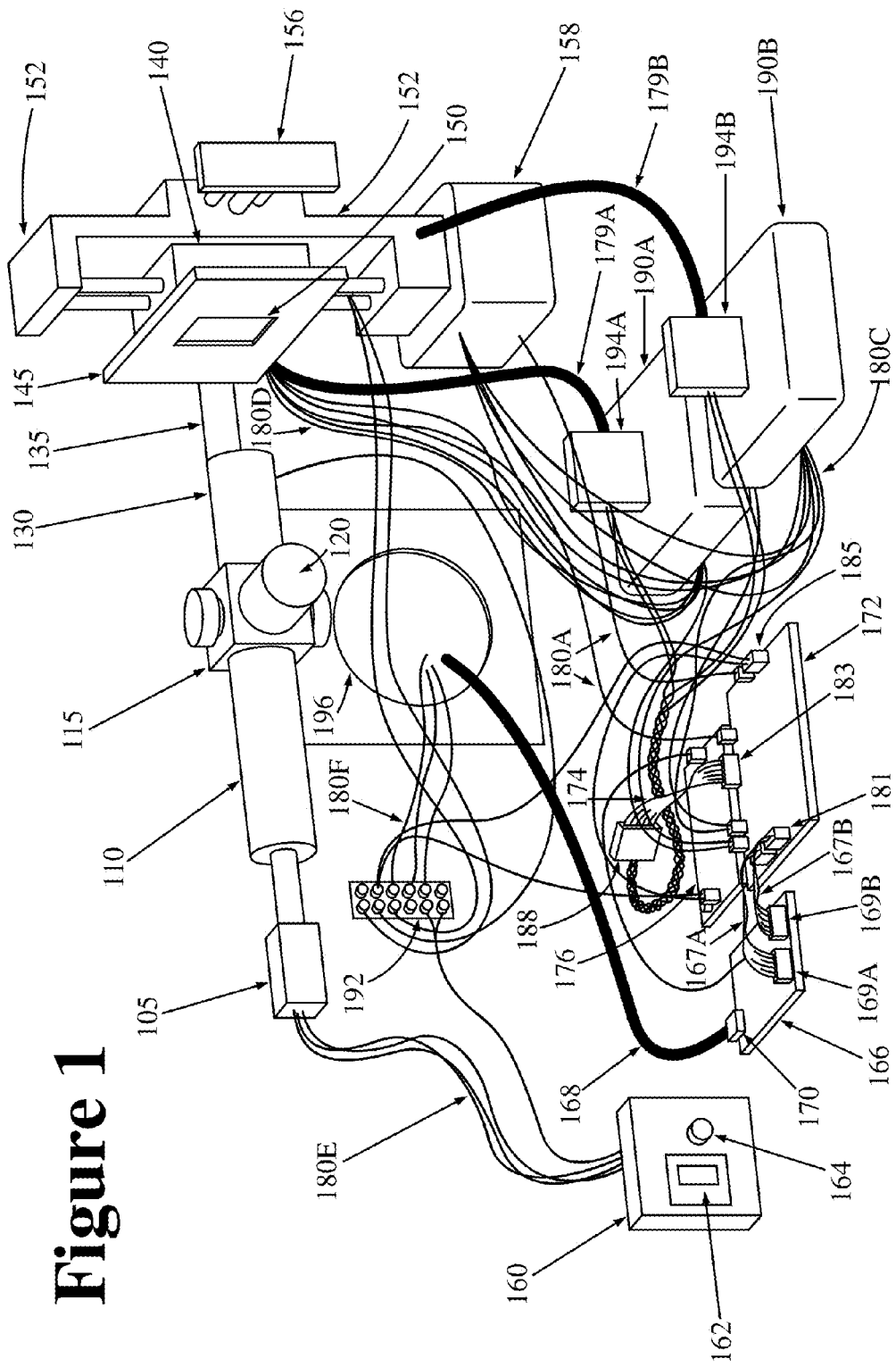
FIG. 1 shows a line drawing of a two-dimensional scanner for nano-second time scale signal detection including a DC terminal block, an optical stack X-Y translation stage and a plate holder according to an embodiment of the invention.

The transitional term 'comprising' is synonymous with 'including,' 'containing,' or 'characterized by,' is inclusive or open-ended and does not exclude additional, unrecited elements or method steps.

The transitional phrase 'consisting of' excludes any element, step, or ingredient not specified in the claim, but does not exclude additional components or steps that are unrelated to the invention such as impurities ordinarily associated with a composition.

The transitional phrase 'consisting essentially of' limits the scope of a claim to the specified materials or steps and those that do not materially affect the basic and novel characteristic(s) of the claimed invention.

As used herein, the term 'high speed switching circuit' is used to describe a transistor that relies on an electric field to control the conductivity of a semiconductor in a circuit. As used herein, the term 'Field Effect Transistor (FET)' is used to describe a specific type of high speed switching circuit.

As used herein, the term 'fluorescence', means emitted light from high performance probes amenable to detection. As used herein, the term 'fluorophore' is used to describe a molecule or component of a molecule including a quantum dot that causes the molecule to be fluorescent. When the fluorophore is a molecule with a component that causes the fluorescence it can be described as labeled (or tagged) with a fluorescent probe. The term 'receiving a fluorophore labeled sample with a half-life' includes preparing a molecule with a component that causes the molecule to be fluorescent and adding or otherwise mixing the fluorescent molecule to a sample to generate the fluorophore labeled sample. The fluorophore can after being excited enter an excited state before emitting energy as a photon.

As used herein, the phrase 'a light source' is used to describe a source that can produce an emission of light. As used herein, the phrase 'a pulse generator' is used to describe a generator that can pulse an emission of light. The term 'producing' an excitation pulse' refers to the process of converting a continuous light source into pulses of light. As used herein, the phrase 'a pulsed light source' is used to describe a light source that can produce single or periodically repeated bursts of light lasting a specific duration of time. The pulse rate is the number of bursts of light per second. With reference to pulse rate, approximately includes a range of plus or minus ten percent of the specified pulse rate. Background light is the ambient light of the system plus any remaining light from the excitation light pulse. An excitation cycle is the time taken for ninety eight (98) per cent of the light to be emitted following a single excitation light pulse. The duration of the light pulse is the time taken for approximately eighty five (85) per cent of the emitted light to dissipate. With reference to light dissipation, approximately includes a range of plus or minus ten percent. The phrase 'single detection period' refers to the light detected following a single excitation light pulse. The phrase 'single excitation cycle' refers to the time taken from the pulse of light to the detection. The phrase 'single gate delay' refers one gate delay period. A single light source pulse refers one excitation light pulse. The phrase 'high speed' means less than 5 nano seconds.

As used herein, the phrase 'active detector' is used to describe a detector to which one or more voltages are applied to generate one or more potentials on one or more surfaces or one or more contacts of the detector to allow the detector to operate continuously during an experiment.

As used herein, the phrase 'active photomultiplier tube' is used to describe a photomultiplier to which one or more voltages are applied to generate one or more potentials on one or more surfaces or one or more contacts of the photomultiplier tube to allow the photomultiplier tube to operate continuously during an experiment.

As used herein, the term 'delay' is used to describe a time interval, where the delay determines the time after a light source pulse before the signal received at the detector is directed to the detector. The term 'lower limit' when used in reference to the delay indicates the shortest delay applied. The term 'upper limit' when used in reference to the delay indicates the longest delay applied.

As used herein, the term 'duration' or 'gate duration' is used to describe a time interval selected to be observed. The duration determines a time interval after the delay for which the fluorescence signal is directed to the active detector. The phrase 'providing a delay generated by a timing circuit' is used to describe the process of generating the delay using the RC timing circuit or an equivalent timing circuit. The duration corresponds to the time after the delay before detection by the active detector ceases. The phrase 'providing a duration generated by a control circuit' is used to describe the process of generating the duration using a BoxCar Integrator with a control circuit or equivalent control circuit.

As used herein, the phrase 'BoxCar Integrator' or 'gated integrator' is used to describe a circuit that integrates a specific section of a repetitive analytical signal over a fixed or defined time window.

As used herein, the phrase 'half-life' is used to describe the time required for one-half of the fluorescence of a fluorophore or other signal to be reduced by one half. With reference to half-life, approximately includes a range of plus or minus ten percent of the specified half-life.

As used herein, the term 'excitation area' is used to describe the target surface excited by a light pulse. The term 'resolution' is used to describe the spatial separation between the excitation areas of two light pulses. The term 'irradiation of the sample' is the portion of the sample encompassed by the excitation area. The term 'step generator' refers to a device capable of moving the target surface and includes verniers, stepping motors and the optical stack X-Y translation stage. The term orienting describes the process of either moving the light source or the sample to allow a different excitation area to be irradiated.

As used herein, the phrase 'dichroic optics' is used to describe a filter which can reflect and/or split light into two or more components with differing wavelengths.

As used herein the phrase 'a light emitting diode' is used to describe a semiconductor diode that emits light when a voltage is applied.

As used herein the phrase 'x, y location' is used to describe a 'x' and a 'y' position at which the fluorescence is measured. Changing the x, y location includes changing the x location for a given y location and/or changing the y location for a given x location. Changing the x, y location over a range of both x and y values generates a two dimensional map of the sample in a 'mapping' process. As used herein the phrase 'image acquisition pixel' is used to describe a physical point in a raster image of the location.

As used herein the phrase 'response time' is used to describe the length of time taken by a system to respond to an instruction. The transit time is the total time for a signal to travel from emission to detection.

As used herein the phrase 'control circuitry' is used to describe the electronic components that trigger the excitation light pulse and enable the detection of the fluorescence. Continuous velocity refers to movement of the detector at or near a constant speed in a specific direction.

As used herein the phrase 'data collection timing circuit independent of the signal being collected' is used to describe a specified fixed data collection start time that can be specified to occur before, during or after an event such as a light pulse used to excite fluorescence. The 'data collection timing circuit independent of the signal being collected' can be fixed to generate a start time to occur before, during or after an event as required.

In an embodiment of the present invention, the wavelength at which the fluorophore absorbs light is used to detect the presence of the fluorophore. In an alternative embodiment of the present invention, the wavelength at which the fluorophore emits light is used to detect the presence of the fluorophore. In the alternative embodiment, detecting the specific emitted wavelength where there is a difference between the excitation wavelength at which the fluorophore absorbs and the wavelength of the emitted light results in an advantage of detecting fluorescence rather than attempting to detect absorption of light of the specific wavelength. As a result, the emission wavelength of the emitted light is observed against an essentially black background. In contrast, in the case of absorption one must detect a decrease in light intensity against a bright background. Thus, while there can be fewer photons with fluorescence they are observed against a very low background, resulting in an improved signal to noise ratio. As a 'rule of thumb', one gains approximately three (3) orders of magnitude in sensitivity when going from absorption to fluorescence measurements.

Background levels are an important consideration in optical spectroscopy measurements. In general, the aim is to exclude the light source from being detected, but not exclude the signal. While fluorescence can reduce the background by separating the excitation and emission wavelengths, there can still be some 'leakage' of excitation light detected by the detector. Part of this 'leakage' is because the optics, such as filters, are not perfect. Cut-off wavelengths are not absolute, but have a slope about their nominal cutoff wavelength. Further, higher performance fluorescent probes tend to have Stokes shifts of only 10-20 nm, resulting in concomitant overlap of the excitation light through the emission optics.

In an embodiment of the present invention, a means of approaching this problem, and further reducing the excitation light to the emission detector, can be to 'off gate' the detection process. In various embodiments of the present invention, this can more readily be carried out with longer lifetime fluorescent probes. In an embodiment of the present invention, the excitation source is pulsed and the detector electronics can remain off or be bypassed until after the excitation pulse has been completed. This effectively removes a great deal of the 'prompt' signal, direct transmission or reflection of the excitation light that can otherwise be detected by the detector, including scattered light. Thus 'off-gating' further improves the S/N (signal to noise) ratio, and can be an important consideration when detecting weak emission signals. The 'off-gating' method can typically be carried out by turning the photomultiplier (PMT) 'on' to collect the gated emission signal. In an embodiment of the present invention, rather than turning 'on' the power to the PMT, this can be accomplished by turning on one stage in the dynode chain that determines the control voltage for the electron cascade stages, internal to the PMT.

This approach becomes more difficult when working with high performance probes, having lifetimes on the 3-4 ns timescale. When working with probes having lifetimes in the 10's to 100's of ns time range, a delay in the 'on gating' of the data collection of 5-10 ns or longer is feasible. However, this approach is unacceptable when working with probes having 3-4 ns lifetimes. Consider that a probe having a 3 ns lifetime is almost completely extinguished with a 10 ns 'on gating' delay. Further, the benefits of 'off gating' to the S/N ratio is not trivial. In an embodiment of the present invention, a S/N ratio of less than 2, more typically approaching unity, can be observed when using a continuous excitation source. In an unexpected result, when the light is pulsed and data collection 'off gated' the S/N ratio for the same conditions increases to greater than 10.

A comparative analysis of the circuit described by Katsuyoshi Yamasaki et al in Rev. Sci. Instr. (1995) 66, 4395-4396 (hereinafter the Yamasaki circuit) and the proposed circuit was undertaken. The differences between the Yamasaki circuit and the proposed circuit (see FIG. 3) hinge upon the practical mechanism of the 74LS221 circuits employed in both, and how they are exploited. In the Yamasaki circuit the 'trigger in' is passed through an LM361 to give the actual trigger signal, which is passed to one trigger input of the 'first' '221' pair. The low signal output from the 'first' '221' is passed to the 'second' '221'. As a result, the Yamasaki circuit has a mandatory 35 nanosecond (ns) delay between the trigger and the data collection window. This delay is determined by the minimum values of the RC timing circuit for the two '221' half circuits. In the case of the Yamasaki circuit, the triggering event initiates the timing functions, and thus it is not possible to 'pretrigger' the delay process to bring the start of the data collection closer to the triggering event.

In the proposed circuit, two '221' timing circuits are employed each IC having two timing circuits. However, they are used differently in each circuit. The proposed circuit uses the trigger input to 'start' three '221' timers (two circuits on the 'first' '221' circuit (320A, 320B) and one circuit of the 'second' '221' 320C (see FIG. 3 and Table IV for listing of components labeled). Two of these '221' timers 320A, 320B are used to determine the start 620 and duration 610 of the emitted light, e.g., light emitting diode (LED) trigger pulse, while the third '221' timer 320C starts the data collection timing (see FIG. 3 and FIG. 6). As a result in the proposed circuit no delay can potentially be selected between the trigger and the start of the data collection/integration signal period. The proposed circuit eliminates the delay, by delaying the start of the LED trigger pulse to bring it to proximity to the data collection period. The second timing circuit on the second '221' 320D is used to determine the duration of the data integration and for data integration. In this case, the triggering event is generated by the timing circuit 332 on 320B, and as the data collection gate is also started at the same time, the start of the data collection 344 on 320C to 350 on 320D can be adjusted 372 (coarse) 371 (fine) to be very close or even simultaneous with the triggering event.

TABLE IV

Figure 3:
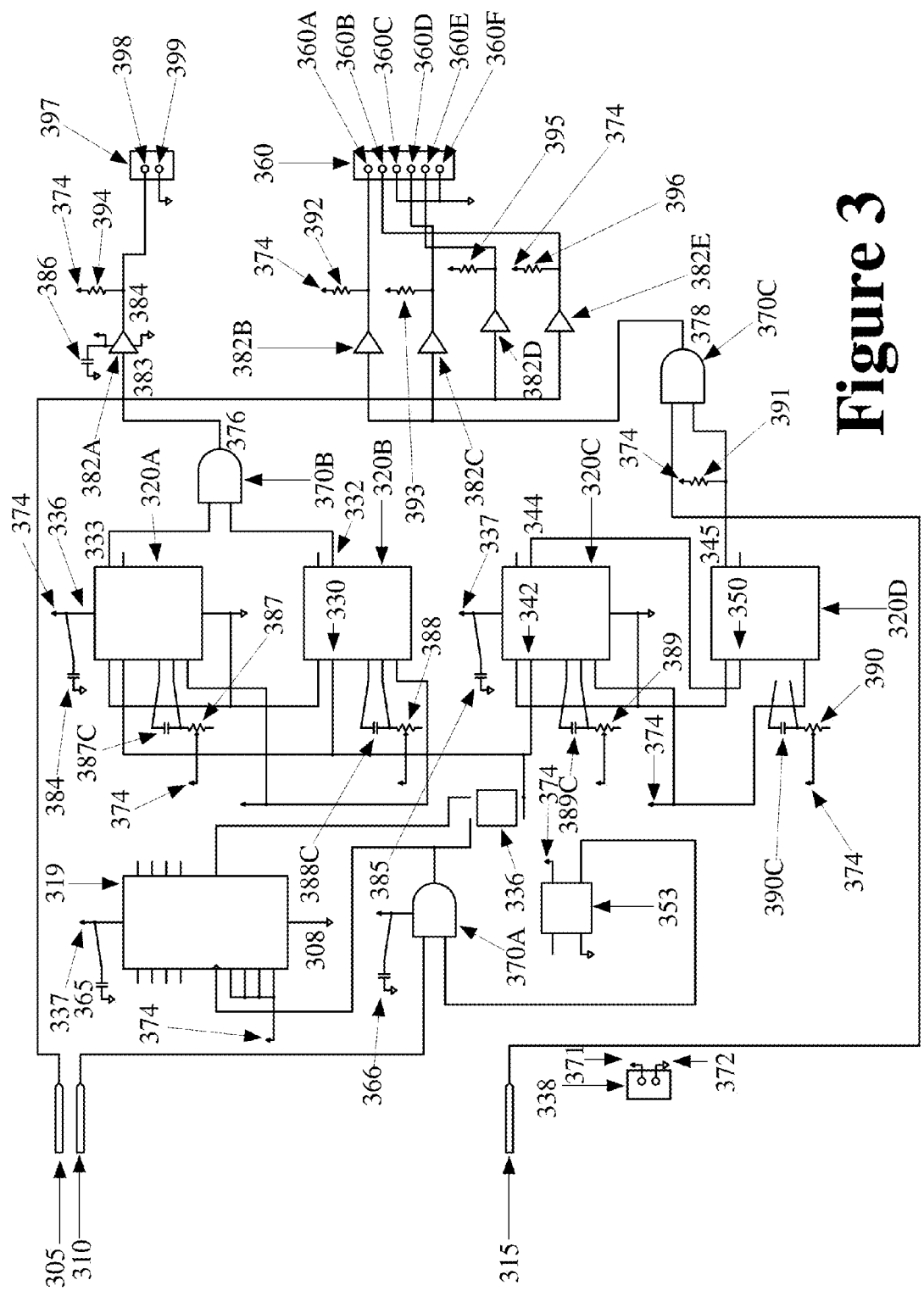
FIG. 3 shows a line drawing of the timing and interface circuit board.

Components Labeled in Pulse and Connection Timing Board (see FIG. 3)

| Label Number | Component corresponding to Label | Connection |
|---|---|---|
| (not labeled on FIG. 3) | /CLR (74LS161 (U2)) | CONNECTED TO +5 v |
| (not labeled on FIG. 3) | >CLK (Data acquisition control (74LS161 (U2)) | |
| (not labeled on FIG. 3) | ENP (FET data acquire switch control (74LS161 (U2)) | CONNECTED TO +5 v |
| 305 | Reset (Pulse Out Enable) | |
| 308 | Ground (74LS161 (U2)) | |
| (not labeled on FIG. 3) | /LOAD (74LS161 (U2)) | CONNECTED TO +5 v |
| 310 | ENT (74LS161 (U2)) | CONNECTED TO +5 v |
| 315 | RCO (74LS161 (U2)) | DIVIDE BY 16 OUTPUT TO JUMPER 336 |
| (not labeled on FIG. 3) | VCC (Capacitor discharge switch) (74LS161 (U2)) | +5 v, CONNECTED THRU 365 |
| (not labeled on FIG. 3) | Pulse Out Enable (Data Collect Enable) | |
| 319 | 74LS161 (U2) | |
| 320A | 74LS221 (U3) (1st half of 1st pair) START | |
| 320B | 74LS221 (2nd half of 1st pair) END | |
| 320C | 74LS221 (1st half of 2nd pair) | |
| 320D | 74LS221 (2nd half of 2nd pair) | |
| (not labeled on FIG. 3) | /A (74LS221 (U3)) | HELD AT GND |
| (not labeled on FIG. 3) | B (74LS221 (U3)) TIMING CYCLE PULSE INPUT | |
| (not labeled on FIG. 3) | /CLR (74LS221 (U3)) | HELD AT +5 V |
| (not labeled on FIG. 3) | C (74LS221 (U3)) - RC TIMING CIRCUIT INPUTS | |
| (not labeled on FIG. 3) | R/C (74LS221 (U3)) - RC TIMING CIRCUIT INPUTS | |
| (not labeled on FIG. 3) | Ground (74LS221 (U3)) | |
| (not labeled on FIG. 3) | /A (74LS221 (U3)) | HELD AT GND |
| 330 | B (74LS221 (U3)) - TIMING CYCLE PULSE INPUT | |
| (not labeled on FIG. 3) | /CLR (74LS221 (U3)) | HELD AT +5 V |
| 332 | /Q (74LS221 (U3)) - trigger period start output (starts at end of low period, when it goes high) | |
| 333 | Q (74LS221 (U3)) - trigger period end output (ends when high output goes low) | |
| (not labeled on FIG. 3) | C (74LS221 (U3)) - RC TIMING CIRCUIT INPUTS | |
| (not labeled on FIG. 3) | R/C (74LS221 (U3)) - RC TIMING CIRCUIT INPUTS | |
| 336 | VCC (74LS221 (U3)) | |
| 337 | +5 v /LOAD INPUT | CONNECTED TO +5 v |
| 338 | J1 | |
| (not labeled on FIG. 3) | 1 (J1) | +5 v SUPPLY IN |
| (not labeled on FIG. 3) | 2 (J1) | SUPPLY GND IN |
| (not labeled on FIG. 3) | /A (74LS221 (U4)) | HELD AT GND |
| 342 | B (74LS221 (U4)) TIMING CYCLE PULSE INPUT | |
| (not labeled on FIG. 3) | /CLR (74LS221 (U4)) | HELD AT +5 V |
| 344 | /Q (74LS221 (U4)) | |
| 345 | Q (74LS221 (U4)) - DATA COLLECT TIME DURATION PULSE END OUT | |
| (not labeled on FIG. 3) | C (74LS221 (U4)) - RC TIMING CIRCUIT INPUTS | |
| (not labeled on FIG. 3) | R/C (74LS221 (U4)) - RC TIMING CIRCUIT INPUTS | |
| (not labeled on FIG. 3) | Ground (74LS221 (U4)) | |
| (not labeled on FIG. 3) | /A (74LS221 (U4)) | HELD AT GND |
| 350 | B (74LS221 (U4)) - TIMING CYCLE PULSE INPUT | FROM 344 |
| (not labeled on FIG. 3) | /CLR (74LS221 (U4)) | HELD AT +5 V |

TABLE IV-continued

Components Labeled in Pulse and Connection Timing Board (see FIG. 3)

| Label Number | Component corresponding to Label | Connection |
|---|---|---|
| 353 | Oscillator - provides train of TTL pulses that drives the pulse generation and data collection functions. Logically AND'ed 370A to produce pulse (routed thru 16 bit counter to further reduce pulse rate when needed) | |
| (not labeled on FIG. 3) | C (74LS221 (U4)) - RC TIMING CIRCUIT INPUTS | |
| 355 | R/C (74LS221 (U4)) - RC TIMING CIRCUIT INPUTS | |
| 356 | VCC (74LS221 (U4)) | |
| 357 | J4 | |
| (not labeled on FIG. 3) | 1 (J4) | |
| (not labeled on FIG. 3) | 2 (J4) | |
| 360 | J3 | |
| 360A | 1 (J3) - DATA COLLECT ENABLE OUT | |
| 360B | 2 (J3) - RESET ENABLE OUT | |
| 360C | 3 (J3) - GND | |
| 360D | 4 (J3) - DATA COLLECT ENABLE OUT | |
| 360E | 5 (J3) - RESET ENABLE OUT | |
| 360F | 6 (J3) - GND | |
| 387C | C1 (10 pF) - PULSE DURATION RANGE CAPACITOR | |
| 388C | C2 (10 pF) - PULSE DURATION RANGE CAPACITOR | |
| 389C | C3 (10 pF) - PULSE DURATION RANGE CAPACITOR | |
| 390C | C4 (800 pF) - PULSE DURATION RANGE CAPACITOR | |
| 365 | C5 (1 uF) - CAPACITOR FOR SUPPLY VOLTAGE NOISE FILTER REDUCTION | |
| 366 | C6 (1 uF) - CAPACITOR FOR SUPPLY VOLTAGE NOISE FILTER REDUCTION | |
| 370A | UI74LS08 - ANDING CIRCUITS - OUTPUT HIGH WHEN BOTH INPUTS HIGH | |
| 370B | UI74LS08 - ANDING CIRCUITS - OUTPUT HIGH WHEN BOTH INPUTS HIGH | |
| 370C | UI74LS08 - ANDING CIRCUITS - OUTPUT HIGH WHEN BOTH INPUTS HIGH | |
| 371 | 1 - DATA COLLECT ENABLE INPUT | |
| 372 | 2 - OSCILLATOR PULSE INPUT | |
| (not labeled on FIG. 3) | 3 - TRIGGER PULSE OUT - used directly or divided to 1/16$^{th}$ rate via jumper 336. | |
| 374 | 4 - trigger period AND input | |
| (not labeled on FIG. 3) | 5 - trigger period AND input | |
| 376 | 6 - trigger out, when 374 & 375 are both high | |
| (not labeled on FIG. 3) | 7 - GND | |
| 378 | 8 - DATA COLLECT PERIOD PULSE | |
| (not labeled on FIG. 3) | 9 - data collect enable in - data collected while 379 and 380 are both high. | |
| (not labeled on FIG. 3) | 10 - data collect time in - when this goes high & 379 is high then data is collected. | |
| (not labeled on FIG. 3) | 14 - | |
| 382A | 74LS07 (U5) - USED AS A LINE DRIVER | |
| 382B | 74LS07 (U5) - USED AS A LINE DRIVER | |
| 382C | 74LS07 (U5) - USED AS A LINE DRIVER | |
| 382D | 74LS07 (U5) - USED AS A LINE DRIVER | |
| 382E | 74LS07 (U5) - USED AS A LINE DRIVER | |
| 383 | 1 (74LS07 (U5)) - trigger in | |
| (not labeled on FIG. 3) | 3 (74LS07 (U5)) | |
| (not labeled on FIG. 3) | 5 (74LS07 (U5)) | |
| (not labeled on FIG. 3) | 9 (74LS07 (U5)) | |
| (not labeled on FIG. 3) | 11 (74LS07 (U5)) | |
| 384 | 2 (74LS07 (U5)) - TRIGGER PULSE OUT | |
| (not labeled on FIG. 3) | 4 (74LS07 (U5)) | |
| (not labeled on FIG. 3) | 6 (74LS07 (U5)) | |
| (not labeled on FIG. 3) | 8 (74LS07 (U5)) | |
| (not labeled on FIG. 3) | 10 (74LS07 (U5)) | |
| 385 | 7 (74LS07 (U5)) - CAPACITOR FOR SUPPLY VOLTAGE NOISE REDUCTION | |

TABLE IV-continued

Components Labeled in Pulse and Connection Timing Board (see FIG. 3)

| Label Number | Component corresponding to Label | Connection |
|---|---|---|
| 386 | 14 (74LS07 (U5)) - CAPACITOR FOR SUPPLY VOLTAGE NOISE REDUCTION | |
| 387 | R1 - PULSE DURATION TIME ADJUSTMENT POTENTIOMETER | |
| 388 | R2 - PULSE DURATION TIME ADJUSTMENT POTENTIOMETER | |
| 389 | R3 - PULSE DURATION TIME ADJUSTMENT POTENTIOMETER | |
| 390 | R4 - PULSE DURATION TIME ADJUSTMENT POTENTIOMETER | |
| 391 | R5 - PULL UP RESISTOR | |
| 392 | R6 - PULL UP RESISTOR | |
| 393 | R7 - PULL UP RESISTOR | |
| 394 | R8 - PULL UP RESISTOR | |
| 395 | R9 - PULL UP RESISTOR | |
| 396 | R10 - PULL UP RESISTOR | |
| 397 | J4 | |
| 398 | | 1 (Trigger Out) |
| 399 | | 2 (To light Flasher) - TRIGGER OUT GND |

Additionally, the width of the data collection period, is determined by the capacitors of the RC timing circuits of the 'second' '221' circuits (circuit 3 320C and circuit 4 320D see FIG. 3). The Yamasaki circuit shows a switch selectable range of capacitances, coupled to a variable resistor, to give a very wide range of data collection times. This makes the Yamasaki circuit more suitable for general applications. The proposed circuit is optimized for collecting data from high performance 'short' lifetime fluorescent probes. As such, it enables the proposed circuit to begin data collection closer to the time of the maximum signal. The proposed circuit data collection start and interval can be varied however by changing the RC values, usually through adjustments to the variable resistors 387, 388, 389 and 390 (see FIG. 3).

Figure 4:
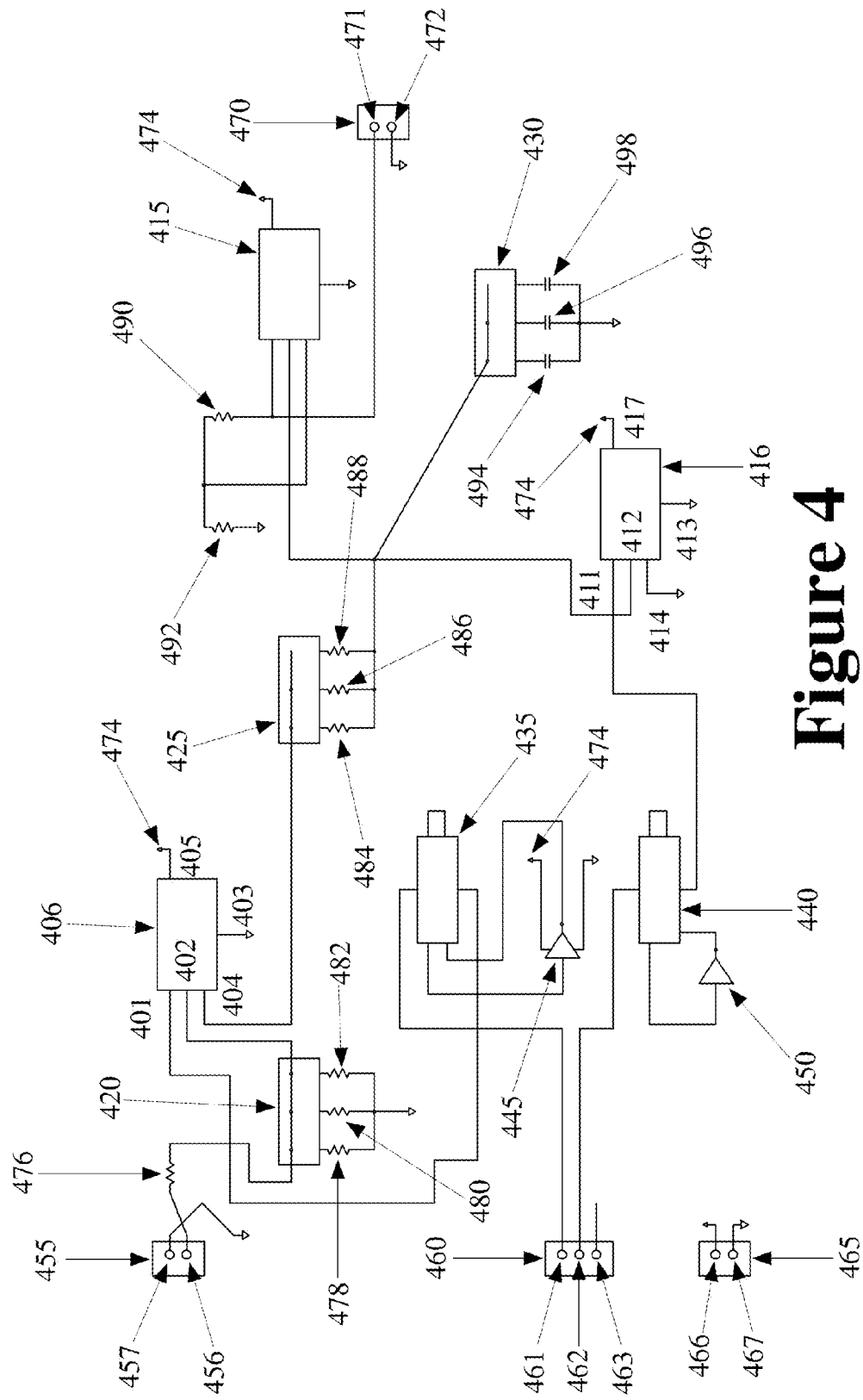
FIG. 4 shows a line drawing of the analog input board.

The complementary metal oxide semiconductor (CMOS) switch shown in the Yamasaki circuit was somewhat slower, with a higher 'on' resistance. In an embodiment of the invention, the switching speed becomes important when measuring signals with less than 4 ns half-life, where the aim is to keep the light source from contributing to the measured fluorescence signal, while not encumbering the measurement of the fluorescence signal. A representative circuit is shown in FIG. 4 (for listing of components labeled see Table V). In an embodiment of the present invention, the signal from the amplifier comes in on Pin 1 of J1, see 461, FIG. 4, and in the absence of a jumper on JP1, see 336, FIG. 3 passes directly to the FET switch. The DCE (data collect enable) signal (pin 1, J2, see 461, FIG. 4), through a logic gate, controls the FET switch. Jumpers are provided if the DCE signal polarity needs to be reversed. When pin 1 of the FET switch goes low the PMT output is connected to an RC circuit, the time constant of which is controlled by jumpers selecting for 391, 392, or 393 and for 387C, 388C, or 389C. The selected time constant determines the number of data collection pulses that can be integrated. The RC circuit presents a summed signal to the LM751 op-amp, the output of which goes via pin 1 of J4 to an external Analog to Digital conversion circuit. At the end of a series of data collection pulses an integrator reset pulse is sent (pin 2, J2, see 462, FIG. 4), which is routed through a logic gate as above to the switch control of a second FET switch. When activated the second FET switch connects the capacitors to ground, discharging them in preparation for the next round of data collection pulses.

TABLE V

Components Labeled in Analog Board (see FIG. 4B).

| Label Number | Component Corresponding to Label |
|---|---|
| 401 | 1 (74CBT1G125 (U1)) - SWITCH ENABLE |
| 402 | 2 (74CBT1G125 (U1)) - SIGNAL IN |
| 403 | 3 (74CBT1G125 (U1)) - GND |
| 404 | 4 (74CBT1G125 (U1)) - SIGNAL OUT |
| 405 | 5 (74CBT1G125 (U1)) - +5 v IN |
| 406 | 74CBT1G125 (U1) |
| 460 | J2 |
| 461 | 1 (J2) - DATA COLLECT ENABLE IN |
| 462 | 2 (J2) - RESET ENABLE IN |
| 463 | 3 (J2) - GND IN |
| 411 | 1 (74CBT1G125 (U2)) |
| 412 | 2 (74CBT1G125 (U2)) |
| 413 | 3 (74CBT1G125 (U2)) |
| 414 | 4 (74CBT1G125 (U2)) |
| 417 | 5 (74CBT1G125 (U2)) |
| 416 | 74CBT1G125 (U2) - connects to gnd and discharges capacitor (448, 449, or 450) when 409 is enabled (goes high). |
| 474 | +5 v |
| 476 | R1 (100) |
| not labeled (see 420 pin 1) | 1 (Jumper JP1) |
| not labeled (see 420 pin 2) | 2 (Jumper JP1) |
| not labeled (see 420 pin 3) | 3 (Jumper JP1) |
| not labeled (see 420 pin 4) | 4 (Jumper JP1) |
| not labeled (see 420 pin 5) | 5 (Jumper JP1) |
| not labeled (see 420 pin 6) | 6 (Jumper JP1) |
| 420 | Jumper Block JP1 - JUMPERS USED TO OPTIONALLY SELECT RESISTORS |
| 478 | R2 (10k) - OPTIONAL RESISTORS FOR CURRENT TO VOLTAGE CONVERSION |
| 480 | R3 (100k) - OPTIONAL RESISTORS FOR CURRENT TO VOLTAGE CONVERSION |
| 482 | R4 (1M) - OPTIONAL RESISTORS FOR CURRENT TO VOLTAGE CONVERSION |
| not labeled (see 425 pin 1) | 1 (Jumper JP2) |
| not labeled (see 425 pin 2) | 2 (Jumper JP2) |
| not labeled (see 425 pin 3) | 3 (Jumper JP2) |

TABLE V-continued

Components Labeled in Analog Board (see FIG. 4B).

| Label Number | Component Corresponding to Label |
| --- | --- |
| not labeled (see 425 pin 4) | 4 (Jumper JP2) |
| not labeled (see 425 pin 5) | 5 (Jumper JP2) |
| not labeled (see 425 pin 6) | 6 (Jumper JP2) |
| 425 | Jumper JP2 - used to select resistance for RC circuit for integrating data |
| 484 | R5 (200) |
| 486 | R6 (700) |
| 488 | R7 (1.6k) |
| not labeled (see 430 pin 1) | 1 (Jumper JP3) |
| not labeled (see 430 pin 2) | 2 (Jumper JP3) |
| not labeled (see 430 pin 3) | 3 (Jumper JP3) |
| not labeled (see 430 pin 4) | 4 (Jumper JP3) |
| not labeled (see 430 pin 5) | 5 (Jumper JP3) |
| not labeled (see 430 pin 6) | 6 (Jumper JP3) |
| 430 | Jumper JP3 - used to select capacitor for RC circuit for integrating data. |
| 494 | C1 (0.001 uf) |
| 496 | C2 (0.01 uf) |
| 498 | C3 (0.1 uf) |
| not labeled (see 435 pin 1) | 1 (Jumper JP4) |
| not labeled (see 435 pin 2) | 2 (Jumper JP4) |
| not labeled (see 435 pin 3) | 3 (Jumper JP4) |
| not labeled (see 435 pin 4) | 4 (Jumper JP4) |
| not labeled (see 435 pin 5) | 5 (Jumper JP4) |
| not labeled (see 435 pin 6) | 6 (Jumper JP4) |
| 435 | Jumper Block JP4 position of the jumpers used to maintain or reverse the polarity of the switching pulse to 401, by routing the signal through the inverter (440). |
| 455 | J1 |
| 456 | 1 (J1) - SIGNAL DATA IN FROM PMT |
| 457 | 2 (J1) - DATA GND IN FROM PMT |
| not labeled (see 1 440 pin 1) | (Jumper JP5) |
| not labeled (see 2 440 pin 2) | (Jumper JP5) |
| not labeled (see 3 440 pin 3) | (Jumper JP5) |
| not labeled (see 4 440 pin 4) | (Jumper JP5) |
| not labeled (see 5 440 pin 5) | (Jumper JP5) |
| not labeled (see 6 440 pin 6) | (Jumper JP5) |
| 440 | Jumper JP5 position of the jumpers used to maintain or reverse the polarity of the switching pulse to 401, by routing the signal through the inverter (450). |
| 465 | J3 |
| 466 | 1 (J3) |
| 467 | 2 (J3) |
| not labeled (see 445 pin 1) | 1 (74LS04 (U4)) |
| not labeled (see 445 pin 2) | 2 (74LS04 (U4)) |
| not labeled (see 445 pin 3) | 3 (74LS04 (U4)) |
| not labeled (see 445 pin 4) | 4 (74LS04 (U4)) |
| 445 | 74LS04 (U4) |
| 450 | 74LS04 (U4) |
| not labeled (see 445 pin 7) | 7 (74LS04 (U4)) |
| not labeled (see 445 pin 14) | 14 (74LS04 (U4)) |
| 415 | LM751 (U3) - INTEGRATED SIGNAL OP AMP. |
| not labeled (see 415 pin 1) | 1 (LM751 (U3)) |
| not labeled (see 415 pin 2) | 2 (LM751 (U3)) |
| not labeled (see 415 pin 3) | 3 (LM751 (U3)) |
| not labeled (see 415 pin 4) | 4 (LM751 (U3)) |
| not labeled (see 415 pin 5) | 5 (LM751 (U3)) |
| 470 | J4 |
| 471 | 1 (J4) Signal Out |
| 472 | 2 (J4) Ground |
| 490 | R8 (2k) |
| 492 | R9 (500) |

In an embodiment of the present invention, the timing of the DCE signal in the current implementation can be determined as an offset from the start of the light pulse signal, through a separate timing and signals interface board. This timing and duration of the DCE signal, as well as that of the duration of the light pulse trigger signal, can be determined by a pair of dual multivibrators (74LS221) IC's on the interface board. The timing relationships can be adjusted by adjusting the values of the timing RC components external to these IC's, specifically the variable resistors 387, 388, 389 and 390 (see FIG. 3). Changes in the timing range, over an approximately 15× range, can be made by changing the values of the timing capacitors in these circuits 387C, 388C, 389C and 390C (see FIG. 3).

In various embodiments of the present invention, use of this approach can be dependent upon the characteristics of the PMT and associated electronics. A prime characteristic is that the PMT must be highly responsive to the light input, both for the rise and even more importantly for the decay times when the light is turned off. The light itself must also have a digital quality in the on and off times, most particularly without a prolonged decay in the off process. In an embodiment of the present invention, between the PMT output and the signal integrator circuit can be a TB-411-8A+ amplifier eval/demo board from MiniCircuits (www.minicircuits.com), which has a MAR-8ASM+ monolithic amplifier as its main component. The amplifier operates from DC to 1 GHz frequency, and gives a + going voltage signal from the − going current output of the PMT. This signal can be gated using the switching IC as described above. The integrator circuit can be gated on for a defined period of time, to collect a specific segment of the PMT output signal following the excitation light pulse, and thus operates as a Box Car Integrator.

In an embodiment of the present invention, an advantage of this approach to gating is that the PMT is always 'on'. As a result the gating process does not require the switching 'on' and 'off' of high voltage power to the PMT, with the attendant circuit design complications and requirements to do this switching. The implementation is simple, direct, and low cost. The approach has considerable flexibility, as with adjustment of the timing parameters one can bring the on gating point to any point prior to, during, or after the switching off of the excitation light source.

In an embodiment the invention relates to a system for measuring the multidimensional distribution of a signal generating substance. In an embodiment, the invention relates to a system for measuring the multidimensional distribution of a protein or other substance. The substance can be tagged with a short life fluorescent label. A sample is scanned with an optical point source excitation and read back optical stage. In an embodiment of the present invention, the sample is excited at each of a plurality of points with a fast, e.g., nanosecond time scale pulse of light and the resulting fluorescence is detected preferably after the excitation is extinguished. In an embodiment of the present invention, the half-life of the fluorescent label is 1-3 nanoseconds. In an alternative embodiment of the present invention, the half-life of the fluorescent label is 3-5 nanoseconds. In another embodiment of the present invention, the half-life of the fluorescent label is 5-9 nanoseconds. In another embodiment of the present invention, the half-life of the fluorescent label is 9 nanoseconds to 1 microsecond. In a further embodiment of the present invention, the half-life of the fluorescent label is 0.4 microseconds. In another alternative embodiment of the present invention, the half-life of the fluorescent label is 1-5 microseconds.

In an embodiment of the present invention, a detection gate window can start at the tail of the excitation and extend for a predetermined amount of time. In an embodiment of the present invention, the excitation points are between 1-10 microns$^2$ in diameter. In an alternative embodiment of the present invention, the excitation points are between 10-50 microns$^2$ in diameter. In an alternative embodiment of the present invention, the excitation points are between 50-100 microns$^2$ in diameter. In an embodiment of the present invention, the pulse rate and data acquisition rate is 1000 pulses per second (pps) with one data sample per pulse. In an alternative embodiment of the present invention, the pulse rate and data acquisition rate is 4,000,000 pulses per second (pps) with one data sample per pulse. In an embodiment of the present invention, a 1 cm by 1 cm sample can be scanned with 4 megasample resolution. In an embodiment of the present invention, in a 4 megasample resolution each pixel corresponds to a 5 micron shift in the excitation area, which in turn can be 50 to 100 microns$^2$ in diameter. In an alternative embodiment of the present invention, in a 4 megasample resolution each pixel corresponds to a 10 micron shift in the excitation area. In various embodiments of the invention, excitation areas can be 200 microns$^2$ down to 1 micron, depending on the optics. The excitation area can become more important when the excitation area is reduced to 5 micron. In an embodiment of the invention, the excitation area can be the same size as the shift in the excitation area corresponding to each pixel. In an alternative embodiment of the invention, the shift corresponding to each pixel can be three times the excitation area. In another embodiment of the invention, the shift corresponding to each pixel can be the ten times the excitation area. The excitation area and the shift corresponding to each pixel can become more important when the excitation area is reduced to 5 micron in order to get blank analysis between each excitation spot analysis. In an embodiment of the present invention, the stage can be moved at a continuous velocity, using a stepper motor with the data being collected by a string of light pulses between motor step pulses to improve the speed of analysis.

In an embodiment of the present invention, the sample can be taken after the excitation is extinguished to remove the excitation from the data sample. The process also reduces noise in the sample data. In an embodiment of the present invention, the system can include dichroic optics to further eliminate the excitation and ambient light from the sample. In an embodiment of the present invention, the system can be housed in a black box to eliminate ambient light. In an embodiment of the present invention, an LED light source can be used for economy and to minimize interference effects. In an embodiment of the present invention, the scanner can be used with U.S. Pat. No. 7,291,459 filed Dec. 10, 2002, inventor Pusey et al., issued Nov. 6, 2007, which is herein expressly incorporated by reference in its entirety.

In an embodiment of the present invention, the sample is captured between a microscope slide and cover and the scan can be two dimensional. In an alternative embodiment, the sample rests on a microscope slide or other suitable surface. In another embodiment of the present invention, the scan can be one dimensional. In an alternative embodiment of the present invention, the scan can be three dimensional using a 2 photon excitation and collect data at the focal point of the optics, where by raising (or lowering) the optics one can scan a plane of points above (or below) the previous data set.

In various embodiments of the present invention, the benefits include direct measurement without having to amplify the protein or gene. Protein (enzymatic, or polymerase chain reaction) amplification can be undesirable because it can contaminate or alter the proportions of the components of the mixture and it can destroy the environment around the protein. In an embodiment of the present invention, the system can observe very low concentrations of the analyte.

These and further benefits and features of the present invention are herein described in detail with reference to exemplary embodiments in accordance with the invention.

SLP Plate Reader

In an embodiment of the present invention, the reader can scan an array of diagnostic spots placed on a substrate. In an embodiment of the present invention, the reader can measure the fluorescence intensity at each point of the scan. In an embodiment of the present invention, the use of a more sensitive detection device results in greater sensitivity of the analyte being detected. In an embodiment of the present invention, the use of photomultiplier tube (PMT) results in greater sensitivity of the analyte being detected. By adjusting the distance between read points (the reading pitch), and keeping the reading pitch smaller than the capture spot size, one can make multiple measurements on a given spot and sum those values for an integrated intensity.

In an embodiment of the present invention, the basic assembly can consist of a fluorescent reader 'optical stack', mounted over a slide holder which can in turn be mounted on an X-Y translation stage (see FIG. 1 and Table III for explanation of labeled components). In an embodiment of the present invention, the optical stack 110, from the bottom up, can include the imaging (and excitation light focusing) objective lens, mounted to a manual focusing stage. Above that a dichroic mirror 115 can be mounted in a rectangular box, followed by a filter holder, having a high pass filter to allow the emitted light but not the excitation light through 115. In an embodiment of the present invention, a spacer tube, can be followed by a lens to focus the light onto the PMT 105, which can be at the top of the stack. In an embodiment of the present invention, coming out of the side of the dichroic mirror holder can be another optical assembly, consisting of an excitation filter, followed by a short spacer, then a focusing/collimating lens, then a LED (the excitation light source) 120. The whole assembly can be mounted in a reduced light enclosure including a light tight box and a plywood box, which can be painted black on the inside to minimize background noise.

TABLE III

Figure 2:
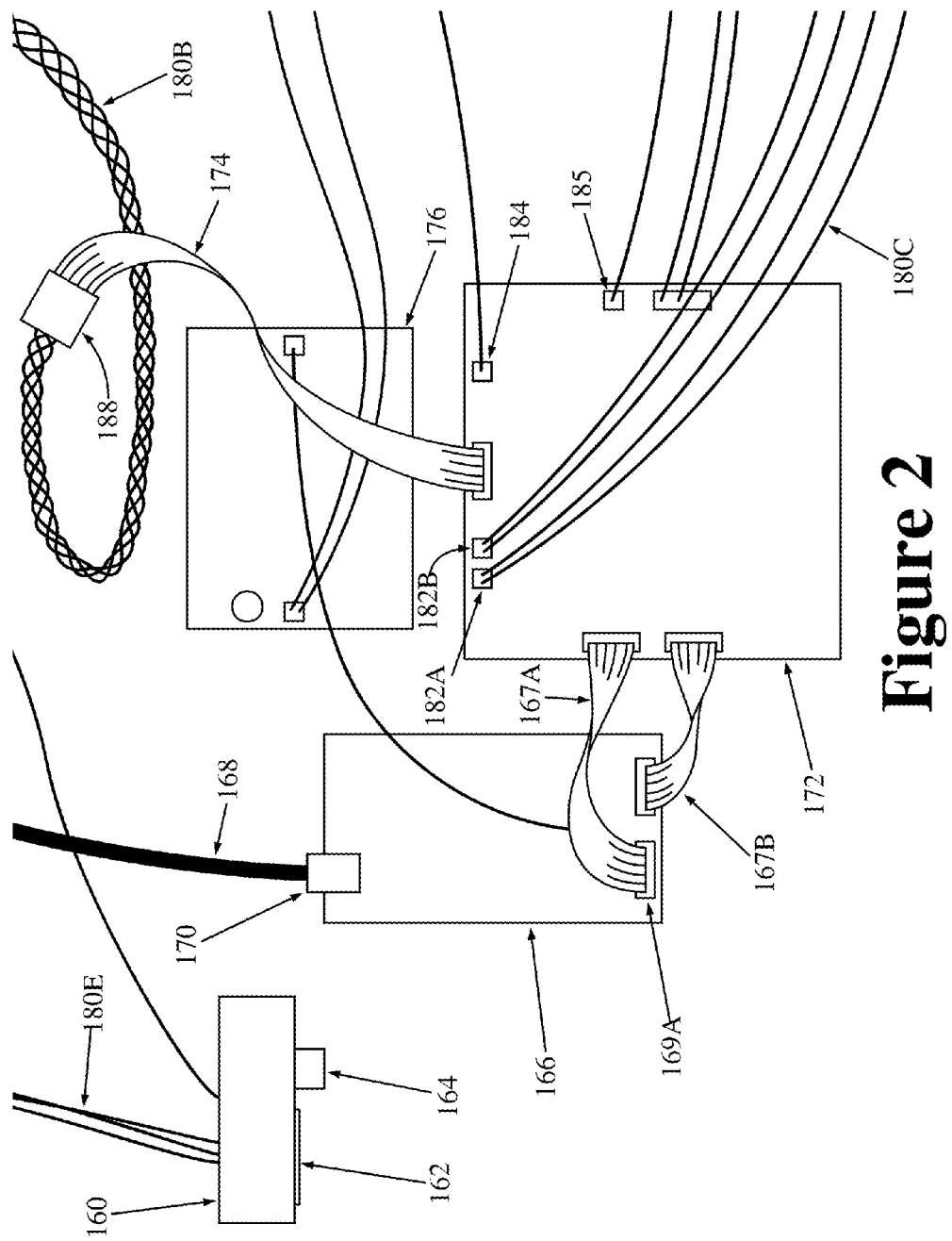
FIG. 2 shows a line drawing of the PMT control microcontroller.

Explanation of Components Labeled in FIG. 1 and FIG. 2.

| Label Number | Component corresponding to Label |
|---|---|
| 105 | Photomultiplier tube (PMT) |
| 110 | Optical stack extension tube with a lens at the bottom |
| 115 | Filter cube - contains excitation & emission filters, dichroic mirror |
| 120 | Excitation light assembly |
| 130 | Microscope objective - see attached notes. |
| 135 | Support rod for the manual focusing stage (vertical axis) |
| 140 | X axis stage that moves |
| 145 | Sample holder |
| 150 | Sample |
| 152 | X - axis translation stage |
| 156 | Y - axis translation stage and connection receptacle for stepper motor |
| 158 | X - axis translation stage and stepper motor |
| 160 | Power control for PMT |
| 162 | Vernier scale for power control - attached to 164. |
| 164 | Power adjustment potentiometer knob for PMT power |
| 166 | Microcontroller board |
| 167A | I/O cables between 169A and 172 |
| 167B | I/O cables between 169B and 172 |
| 168 | USB cable that connects microcontroller to host PC |
| 169A | Table I, I/O cables & connectors from 166 to 172 |
| 169B | Table II, I/O cables & connectors from 166 to 172 |
| 170 | USB connection to microcontroller boards |
| 172 | Timing & signals interface board |
| 174 | Wires connecting 188 to 183 |
| 176 | Analog data acquisition board |
| 178 | Signal input from PMT to analog data acquisition board. |
| 179A | Wires connecting the Y stepper motor 156 to the Y stepper driver control 194A |
| 179B | Wires connecting the X stepper motor 158 to the X stepper driver control 194B |
| 180A | Wires connecting the stepper drivers to 172 |
| 180B | Wires connecting the stepper drivers to 192 |
| 180C | Wires connecting the stepper drivers to 182 and 192 |
| 180D | Wires connecting the stepper drivers to 188 |
| 180E | Wires connecting the PMT 105 to the power control 160 |
| 180F | Wires connecting the stepper drivers to 192 |
| 181 | I/O cables & connectors from 166 to 172 |
| 182A | I/O cables & connectors from 172 to 190A |
| 182B | I/O cables & connectors from 172 to 190B |
| 183 | I/O cables & connectors from 172 to 188 |
| 184 | I/O cables & connectors from 172 to 190A and 190B |
| 185 | I/O cables & connectors from 172 to 192 |
| 188 | Connector between 172 and 183 |
| 190A | X axis Stepper motor driver |
| 190B | Y axis Stepper motor driver |
| 192 | Power distribution connectors |
| 194A | Translation stage limit switch cable connection to the limit inputs on the timing/interface board |
| 194B | Translation stage limit switch cable connection to the limit inputs on the timing/interface board |
| 196 | Opening for leads coming into and out of the box. |

In an embodiment of the present invention, the controlling electronics and the stepper motor drivers, for the X-Y stages, can be mounted directly onto the box, while the trigger, data collection, and microcontroller that run the instrument can be mounted on a swing out plastic panel to facilitate access to the circuit boards. The DC power (5V and 15V) can be supplied by a power supply on top of the box, which can be turned on by a thumb switch in the AC line to the plug. The DC power can be brought into the box through an access hole in the back 196, connecting to a terminal block 192 in the back of the box (see FIG. 1). The 15V power and ground are on the left side of the block, while the 5 V power and ground are on the right 4 positions. The ground can be common to both 15 V and 5 V. The USB cable that interfaces the host PC to the system can also come in through the access at the back 196 of the box.

The systems operation can be controlled by a microcontroller 166 (www.coridiumcorp.com) through a USB interface 168, 170 to the host system (not shown). In an embodiment of the present invention, the microcontroller gains better timing control over the systems operation through use of a 'simpler' microprocessor. In an embodiment of the present invention, the microcontroller renders the instrument more independent of the host system and/or operating system.

In an embodiment of the present invention, the stepper motor controllers can be commercially supplied units requiring two control inputs, one for direction and one for step. In an embodiment of the present invention, the stepper motor can have four outputs that connect to the stepper motor leads, designed for use with bipolar stepper motors. In an embodiment of the present invention, the stepper motor can have switches which can be used to set the limiting current to the stepper motors, as well as the step size (full, half, quarter, etc.). In various embodiments of the present invention, other means can be used to control the stepper motor limiting current and step size. In an embodiment of the present invention, the setup can move one (1) full step for each step pulse (positive signal input). As the lead screws of the translation stages have a one (1) mm pitch, and the motors have 200 steps/revolution, then one step moves the stage 0.005 mm (5 microns). In an embodiment of the present invention, this is more resolution than is required. In an alternative embodiment of the invention, the translation stage lead screws driven by the stepping motors can have a greater pitch in order to speed up the scanning process.

FIG. 2 shows a line drawing of the data acquisition control boards. In an embodiment of the present invention, at the top of the control boards can be mounted a 10 kΩ potentiometer, used to control the voltage, and thus sensitivity, of the PMT. In an embodiment of the present invention, to the right of the microcontroller can be the USB cable, which can connect the system to the host computer. The microcontroller can have 16 digital IO's and 8 A/D inputs, as outlined in Table I and Table II. The first 8 of the digital IO's (0 thru 7) are used to control the spatial position of the light source. In various embodiments of the present invention, other microcontrollers, having more or fewer digital IO's (with additional interface circuitry as needed can be employed.

TABLE I

Connections of microcontroller circuit 169A, see FIG. 1.

| IO line | Control |
|---|---|
| 0 | X stepper direction |
| 1 | X step |
| 2 | Y stepper direction |
| 3 | Y step |
| 4 | LED pulse trigger (when high) |
| 5 | Data integrate enable (when high) |
| 6 | Integrator reset (when high) |
| 7 | Spare IO line. |

TABLE II

Connections of microcontroller circuit 169B, see FIG. 1.

| IO line | Monitors |
|---|---|
| 8 | Not used |
| 9 | X far travel limit switch |
| 10 | X near travel limit switch |
| 11 | Y far travel limit switch |
| 12 | Y near travel limit switch |
| 13 | Spare input |
| 14 | Spare input |
| 15 | Not used |

In an embodiment of the present invention, both the output and input lines can operate through the timing & interface board. The 8 outputs and 6 inputs can be connected to the board through an 8 and 6 conductor ribbon cable, respectively. The lowest number line of each (0 and 9, respectively) can be marked with a piece of yellow shrink tubing. Outputs 0 through 5 can be buffered through a 74LS07 non-inverting driver 382B (see FIG. 3). The outputs of IO lines 0-3 and 7 can be connected to three double pin connectors on the upper right side of the board (see FIG. 2). In descending order these are the X stepper, Y stepper, and spare IO lines respectively. IO lines 4, 5, and 6 can have their outputs on the connectors at the bottom of the board. The two pin connector can be the eventual output for the LED pulse trigger, while the 6 pin plug can have the (eventual) outputs for lines 5, 6, ground, 5, 6, and ground, going from right to left on the plug as shown in FIG. 2. The last two signal connections on the timing and interface board can be the 6 and 2 pin connectors on the lower right side and a 2 pin connector on the upper left side. The upper left connector can be the DC power connection. The 6 pin can be for IO lines 9 thru 12 (top down), with the bottom two pins being+5V out. These provide the voltage levels that keep the inputs of the 74LS04 (not shown) on the board at a high level, with a corresponding low output to the microcontroller. The stage limit switches can be of the NC type. The limit switches are mechanically activated switches that result in a signal being sent to the appropriate circuit, in this case resulting in the cessation of the driving pulses being sent to the stepping motor. The signal can also serve to establish a '0' or reference starting point for that axis. When they are activated they can become open and the 74LS04 outputs go high, signaling a limit has been reached to the microcontroller.

Figure 5:
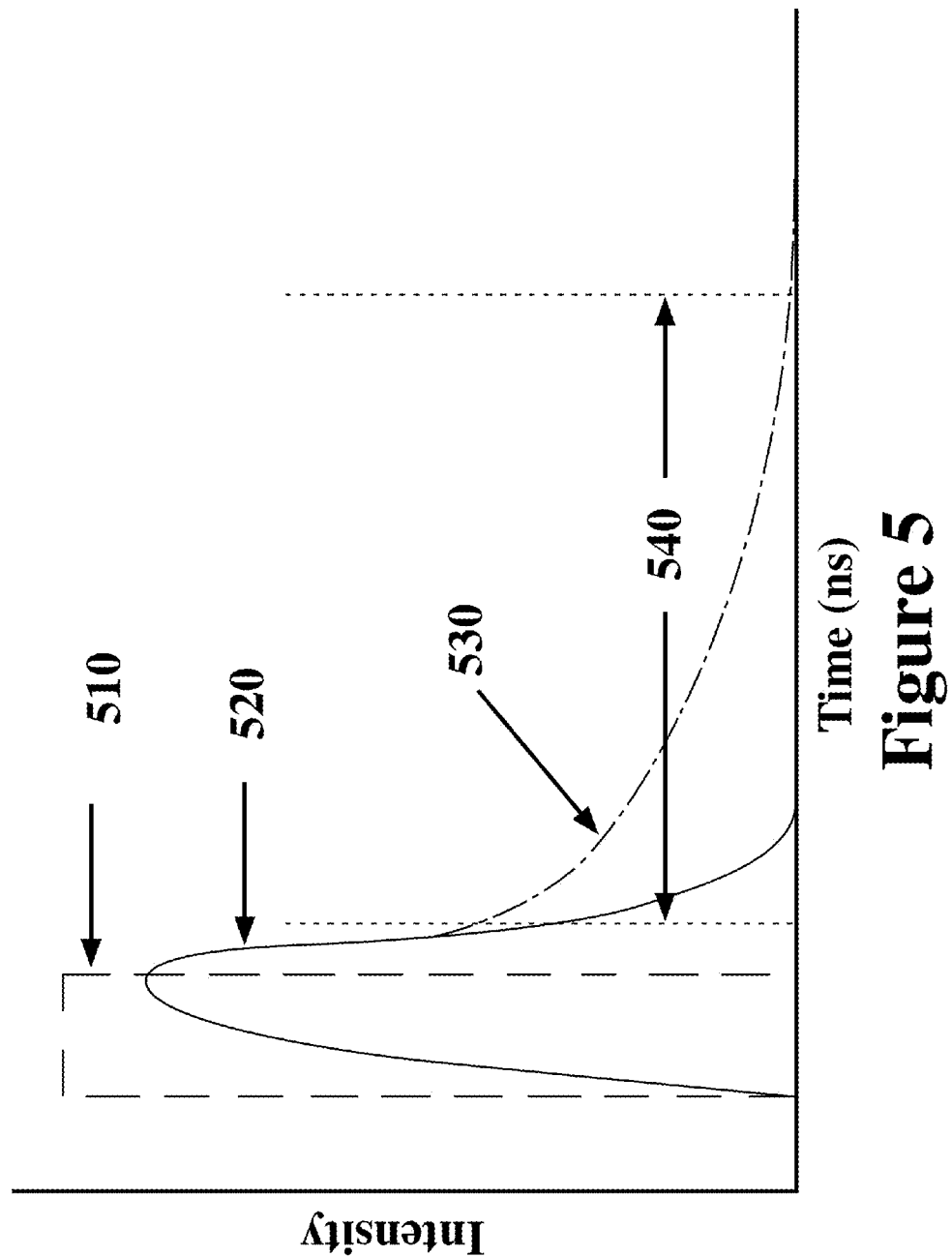
FIG. 5 shows a diagram of the output excitation light pulse width, the intensity of the emitted fluorescence and the gate duration, according to an embodiment of the invention.
Figure 6:
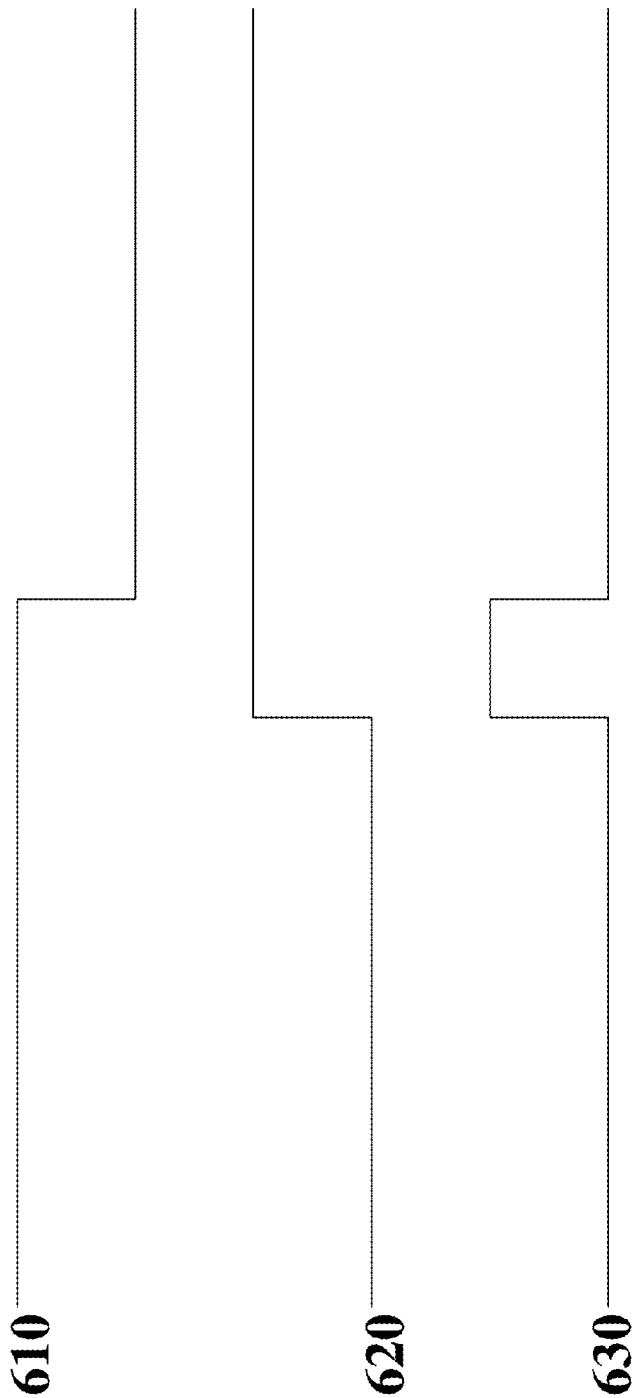
FIG. 6 shows a schematic diagram of the output excitation light pulse width according to an embodiment of the invention.

The schematic for the timing and interface board is shown in FIG. 3 (note that FIG. 3 does not show the 74LS04 interface circuits) according to an embodiment of the invention. While the stage drivers and inputs can operate directly through the 74LS07 382A and 74LS04 (not shown) circuits to the output plugs, the data acquisition controls do not operate directly through the 74LS07 and 74LS04 circuits. A 4 MHz oscillator can generate continuous pulses, feeding directly to a 74LS08 AND 370B circuit (see FIG. 3 and Table IV). The LED pulse trigger (IO4) 330 can control the output of this circuit. The duration of the input high signal on IO4 330 determines the number of pulses sent out during a data collection cycle. In an embodiment of the present invention, when the circuit goes high the oscillator pulses go through, and they can be routed to a 74LS161 4 bit counter 319. A jumper can be used to select either the direct pulses or the divided by 16 pulses for the trigger output. The selected pulse goes to the inputs of 3 of the 4 74LS221 multivibrator circuits 320A, 320B and 320C. The first two of these 320A and 320B determine the output excitation light pulse width 510, as shown in FIG. 5 generated from 610 ANDed with 620 to give 630, as shown in FIG. 6. The duration of the high pulse from Q and the low pulse from $\overline{Q}$ are set by trimpots 387, 388 and trimpots 389, 390 and fed into a logical AND gate 370B (see FIG. 3). In an embodiment of the present invention, during the overlapping period when both the outputs of 320A and 320B are high the output of the gate circuit is also high, thus the start time and duration of the output pulse can be set by adjusting the values of trimpots 389, 390 and trimpots 387, 388 respectively. The 74LS08 370B output then goes to an output 74LS07 driver 382A, which outputs the excitation driver pulse.

FIG. 7 shows the output timing signals from the circuit shown in FIG. 3B, where 710 shows the signal from 308 which triggers the output shown as 720 (representing the signal from 333), 730 (representing the signal from 332), and 740 (representing the signal from 376). The signals shown in 720 and 730 are logically ANDed thru 370B to give the output signal shown as 740. The rising edge of 750 triggers the output shown as 760, which is logically ANDED with 770 to give the signal shown as 780. The duration of the pulses from 333, 332, 344, and 345 are variable by approximately 15 fold by adjustment of the potentiometers 387, 388, 389, and 390 respectively. The time duration range over which this variation can be made is determined by the values of the capacitors 387C, 388C, 389C, and 390C respectively.

In an embodiment of the present invention, the oscillator pulses can also be directed every 250 nanoseconds to the 74LS221 multivibrator 'in' on pin 342 and 'out' on pin 344 of 320C. The $\overline{Q}$ output 344 is used from this circuit to trigger the second half of the multivibrator 'in' on pin 350 'out' on pin 345 of 320D into 370C (triggering on the rising edge). The first half 320C can be used to set the delay time for the data collect enable pulse, while the second half 320D can be used to set the data collection time interval, both adjustable by trim pots R3 389 and R4 390 respectively. The data collection time pulse from the second half 320D can also be ANDed with IO5 370C. The output of the AND circuit 378 can be split and passed thru two 74LS07's 382B, 382C, 382D and 382E allowing the driving of two separate analog data collection boards. Note that the light flash triggering can be carried out independently of the data collection (i.e., with IO4 high), but data collection requires that both IO4 370B and IO5 370C be high.

The reset signal (IO6) is split and goes to two 74LS07's 382B, 382C, 382D and 382E, thence directly to the corresponding output pins. When they go high they close a switch that connects the capacitors of the integrator circuits to ground, thus discharging the capacitance.

The function of the triggering operational amplifier (LM361) of Yamasaki et al. and is accomplished by the timing board. The switching circuits (CMOS 74HC4016) can be replaced by the FET switch, as they have lower 'on' resistance and considerably faster switching times. The input op amp has been removed and the output op amp replaced with an LM751 415, which only requires a +5V power supply (vs. ±18 V for the LF356). Finally, the output time constant resistor-capacitor circuits are removed, with the output going directly to the ADO input of the microcontroller.

The input LF356 was removed to more directly connect the input signal 178 from the PMT 105 to the integrator. The LF 356 has a bandwidth of ~5 MHz, which does not enable accurate reporting of the signal within the data collection time frame. Instead, a TB-411-8A+ amplifier board (www-.minicircuits.com, S/N 833901017) was used to invert the negative connecting to the PMT 105 signals and couple the PMT 105 to the data acquisition circuit 176. To keep the PMT 105 sourced signal in better correspondence to that being integrated, the op amp can be removed and the signal passed thru a current to voltage converter. The 1MΩ input resistor 482 to ground is kept, and the options of using a 100,000 KΩ 480 or 10,000 KΩ 478 instead implemented by a jumper block 420. These resistors act as a current (the PMT output) to voltage converter. In the absence of the jumper a direct signal can be inserted on the top of the block for testing the circuit function. The signal then goes to the 74CBF1G125 switch 406, controlled by the data collect enable in line. As the switch is active (conducts) when low, the high signal from the DCE in is routed through a 74LS04 hex inverter 440 to change it to the required low output. A jumper block is used to select whether this state change is made or not 435. The signal passing through the switch then goes to the integrator part of the circuit, as proposed in the Yamasaki circuit. Also as with the Yamasaki circuit the integrator is directly connected to the output op amp. It is also connected to a second 74CBF1G125 416, such that when the reset input goes high (also routed thru a 74LS04 as above) the integrator capacitor is grounded out to reset the accumulator.

One of the major advantages of fluorescence detection analysis, is the increased sensitivity over absorption methods, is due to the excitation light being at a different wavelength than the measured emitted light. This results in the emitted light being seen against a very dark background, increasing the signal level relative to the noise (of the exciting light). However, the Stokes shift, the difference between the excitation and emission maxima, particularly for higher performance fluorescing molecules, is relatively small, typically on the order of 15-25 nm. Thus with most optics systems a small amount of excitation light gets through. While not a problem with strong signals, with weaker signals this contributes to the noise, lowering the signal to noise ratio.

A means of alleviating this problem is to remove as much of the excitation light as possible from the signal. For CW systems the excitation light is a constant part of the measured signal. By off gating the data collection 510, as shown in FIG. 5, a major part of the excitation light 520 can be removed from the measured emission light 530, thereby reducing the noise and improving the signal to noise ratio. Additionally, by only collecting the data during a defined period of time 540 more of the background noise can be removed.

The present invention has been described above with the aid of functional building blocks illustrating the performance of specified functions and relationships thereof. The boundaries of these functional building blocks have been arbitrarily defined herein for the convenience of the description. Alternate boundaries can be defined so long as the specified functions and relationships thereof are appropriately performed. Any such alternate boundaries are thus within the scope and spirit of the claimed invention. One skilled in the art will recognize that these functional building blocks can be implemented by discrete components, application specific integrated circuits, processors executing appropriate software and the like or any combination thereof.

Example

An experiment to determine the sensitivity of the Fluorescent two-dimensional scanner for signal detection was undertaken to ascertain whether detection of fM (femtomolar) concentration solutions was feasible.

Figure 8A:
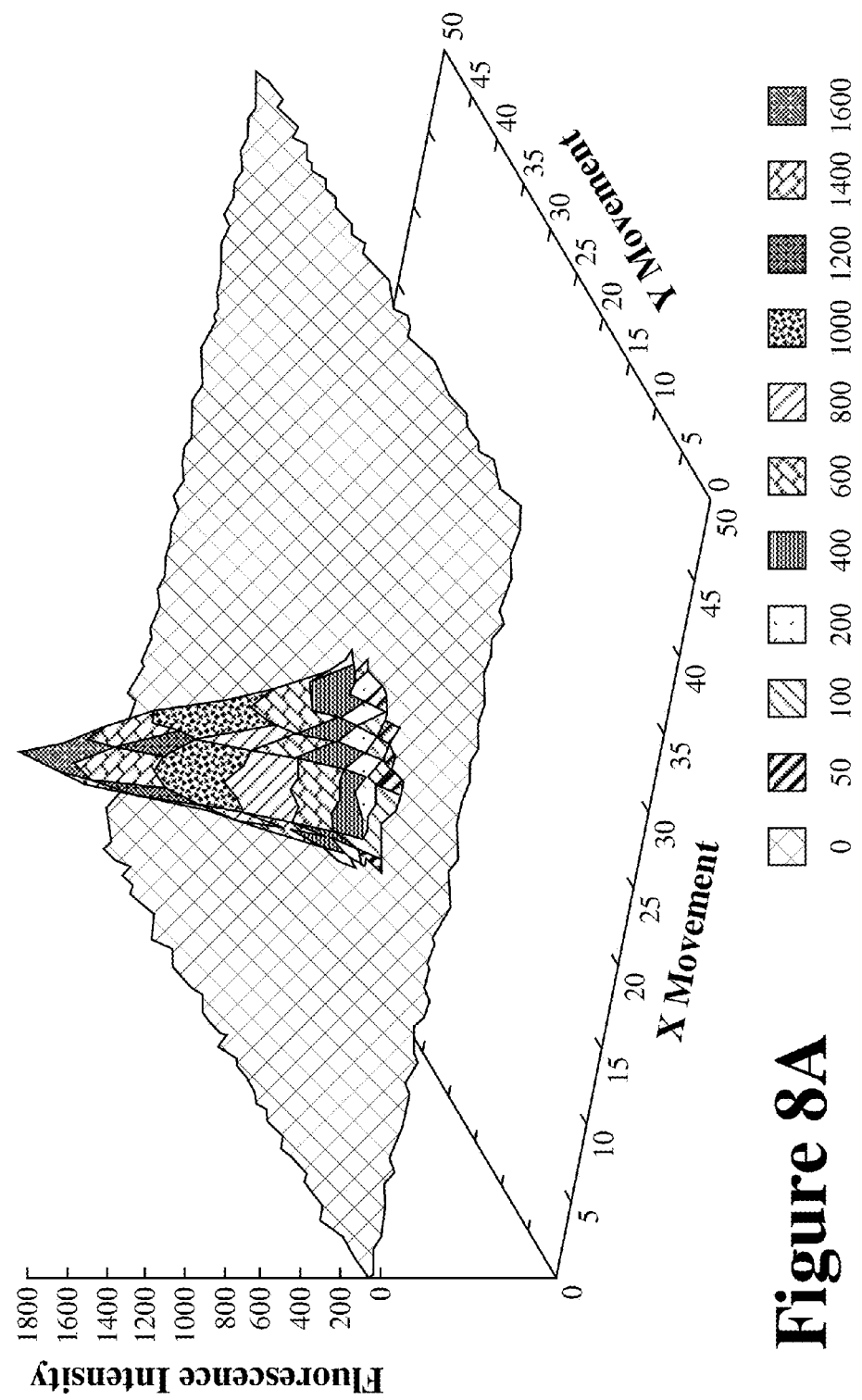
FIG. 8 shows a schematic plot of fluorescent intensity as a function of both X and Y directions for (A) a one picomolar concentration and (B) a one femtomolar concentration solution spotted and scanned according to an embodiment of the invention.
Figure 8B:
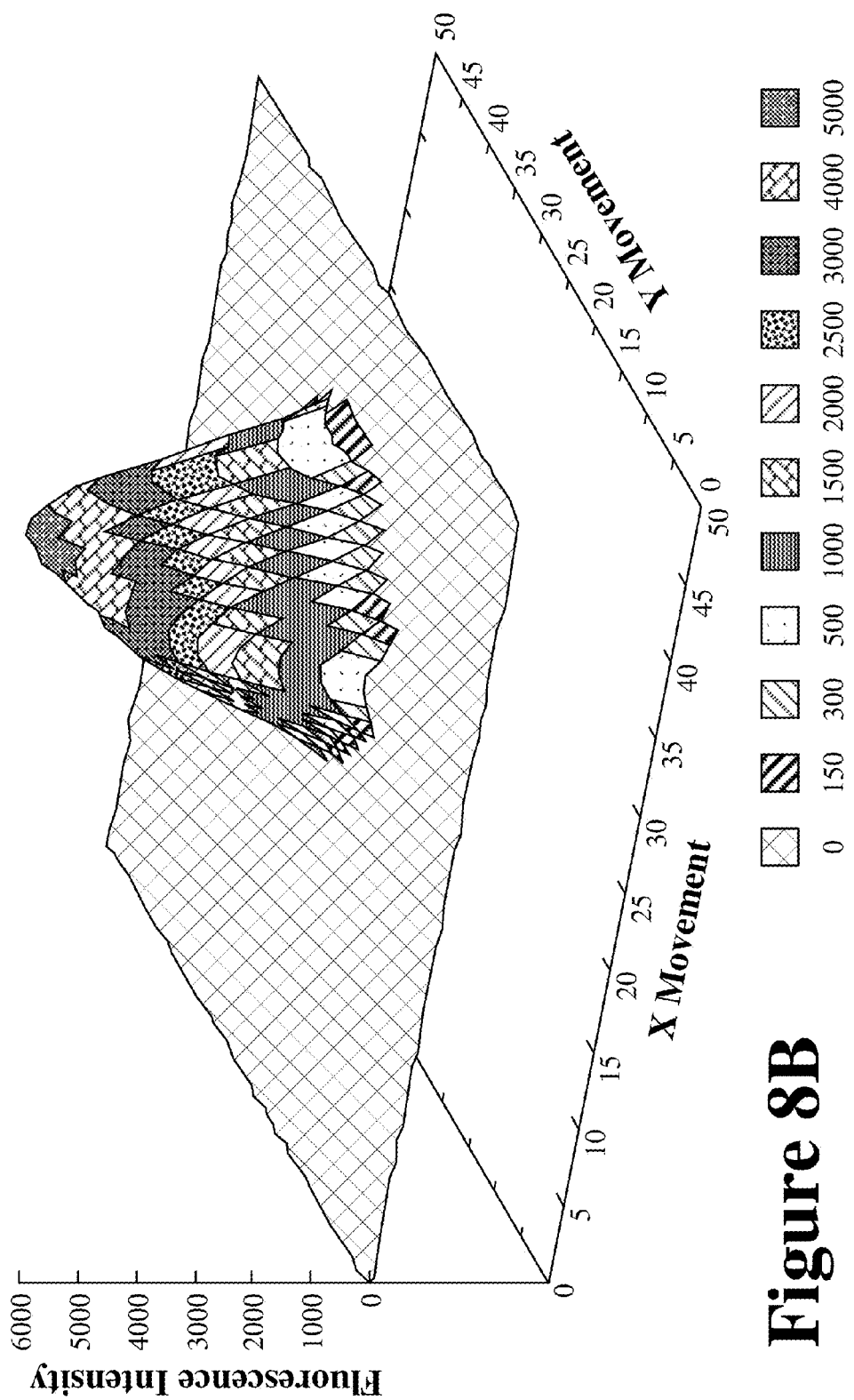

A black anodized aluminum plate was modified by forming wells using a center punch. The wells were approximately 0.5 mm in width and height. The samples included known amounts of the fluorescent marked synthetic dye 'Alexa Fluor 647' (Invitrogen, Carlsbad) in a buffer with no other genetic material. The samples were placed in buffer with no other genetic material. A calibrated stock solution was initially prepared. The stock solution was diluted generating 10 picomolar (pM), 1 pM and 1 femtomolar (fM) concentration sample solutions. Blank control aliquots with just buffer solution were also analyzed. An aliquot (0.5 microliter) of each sample solution and the blank controls were transferred into the wells by hand pipette and allowed to dry. Each sample and the blank controls were then scanned using the Fluorescent two-dimensional scanner at a 5 micron resolution (for both X and Y directions) generating a data set. Each data set consisted of 2500 data points, covering both the black anodized surface and the wells. The blank control spots (with the buffer solution only) revealed an average maximum intensity of 170. This value (170) was used as a 'background' and the values obtained in each sample solution scan were corrected for this background fluorescence. In FIG. 8, where the sample solution spots had fluorescence above the background level, the measured intensities from five (5) scans were added and the fluorescent intensity is plotted as a function of both the X and Y directions changed for each sampling. As shown from a comparison of FIG. 8A and FIG. 8B, as the dye concentration increases, the measured fluorescent intensities increase. The spots that were measured, show different intensities reflecting the spread of the dye across the area. Fluorescence was observed above the background for the 10 picomolar (pM) concentration spots (data not shown). As shown in FIG. 8, fluorescence was observed above the background using the Fluorescent two-dimensional scanner for the 1 picomolar (pM) concentration. Unexpectedly, fluorescence was also observed above the background using the Fluorescent two-dimensional scanner for the 1 femtomolar (fM) concentration spots. In FIG. 8, the different shaded areas are used to quantitatively represent the fluorescence observed. In FIG. 8A, the cross hatched area corresponds with 0 (zero); left bold diagonal corresponds with 50; right diagonal—100; dotted—200; horizontal—400; left herringbone—600; left diagonal—800; bold dotted—1000; shaded dotted—1200; right herringbone—1400; and white dotted—1600. In FIG. 8B: the cross hatched area—0; left bold diagonal—150; right diagonal—300; dotted—500; horizontal—1000; left herringbone—1500; left diagonal—2000; bold dotted—2500; shaded dotted—3000; right herringbone—4000; and white dotted—5000. For the summed analysis of the 1 pM solution, a maximum fluorescence value of 5241 was observed (see FIG. 8A). For the summed analysis of the 1 fM solution, a maximum fluorescence value of 1741 (see FIG. 8B) was observed. Based on this analysis, it was unexpectedly concluded that the Fluorescent two-dimensional scanner was sensitive to the presence of as few as five hundred dye molecules.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

In an embodiment of the invention, a device for identifying a fluorescence signal from a sample comprises a pulsed light source which excites the fluorophore in the sample, a detector operated continuously in operational mode, a Field Effect Transistor (FET) switch controlled by a timing circuit to set a delay between the light source pulse and the commencement of detection, where the delay is a gate start and control circuitry to generate a gate duration, where the fluorescence signal of the fluorophore is detected by the detector directly after the gate start and during the gate duration. In an alternative embodiment of the invention, a device for identifying a fluorescence signal from a sample comprises a pulsed light source which excites the fluorophore in the sample, a detector operated continuously in operational mode, a Field Effect Transistor (FET) switch controlled by a timing circuit to set a delay between the light source pulse and the commencement of detection, where the gate start occurs before the pulse ends and control circuitry to generate a gate duration, where the fluorescence signal of the fluorophore is detected by the detector after the gate start and during the gate duration.

In an embodiment of the invention, a device for identifying a fluorescence signal from a sample comprises: a light source directed at a sample containing a fluorophore which generates a fluorescence signal; a pulse generator to produce a light source pulse; an active detector; a timing circuit used to generate a delay, where the delay determines the time after the light source pulse before the signal received at the detector is directed to the detector; a control circuitry used to generate a duration, where the duration determines a time interval after the delay for which the signal received at the detector is directed to the active detector; and a switch controlled by one or both the delay and the duration to selectively direct a component of the fluorescence signal to the detector, where the fluorescence signal is detected by the detector after the delay and during the duration.

In an embodiment of the invention, a method for detecting a fluorophore labeled sample comprises: applying voltages to a photomultiplier tube (PMT) to enable continuous detection; irradiating the fluorophore labeled sample with a pulse of light; providing a delay generated by a timing circuit, where the delay corresponds to the time after the pulse of light before commencement of detection by the PMT; providing a duration generated by a control circuit, where the duration corresponds to the time after the delay before detection by the PMT is ceased; directing fluorescence from the fluorophore labeled sample using a switch, where the switch directs the fluorescence after the delay and for the duration to the PMT; and detecting the fluorescence of the fluorophore with the PMT.

A device for identifying a fluorescence signal from a sample comprising: a light source directed at the sample containing a fluorophore which generates the fluorescence signal; a pulse generator to produce a light source pulse; an active detector; a timing circuit to generate a delay; a control circuit to generate a duration; and a switch controlled by one or both the delay and the duration to selectively direct the fluorescence signal to the active detector, where the fluorescence signal is detected by the active detector after the delay and during the duration.

A device for identifying a fluorescence signal from a sample comprising: a light source directed at the sample containing a fluorophore which generates the fluorescence signal; a pulse generator to produce a light source pulse; an active detector; a timing circuit to generate a delay; a control circuit to generate a duration; and a high speed switch controlled by one or both the delay and the duration to selectively direct the fluorescence signal to the active detector, where the fluorescence signal is detected by the active detector after the delay and during the duration.

A device for identifying a fluorescence signal from a sample comprising: a light source directed at the sample containing a fluorophore which generates the fluorescence signal; a pulse generator to produce a light source pulse; an active detector; a timing circuit to generate a delay; a control circuit to generate a duration; and a Field Effect Transistor switch controlled by one or both the delay and the duration to selectively direct the fluorescence signal to the active detector, where the fluorescence signal is detected by the active detector after the delay and during the duration The foregoing description of embodiments of the methods, systems, and components of the present invention has been provided for the purposes of illustration and description. It is not intended to be exhaustive or to limit the invention to the precise forms disclosed. Many modifications and variations will be apparent to one of ordinary skill in the relevant arts. For example, steps performed in the embodiments of the invention disclosed can be performed in alternate orders, certain steps can be omitted, and additional steps can be added. The embodiments were chosen and described in order to best explain the principles of the invention and its practical application, thereby enabling others skilled in the art to understand the invention for various embodiments and with various modifications that are suited to the particular used contemplated. Other embodiments are possible and are covered by the invention. Such embodiments will be apparent to persons skilled in the relevant art(s) based on the teachings contained herein. The breadth and scope of the present invention should not be limited by any of the above-described exemplary embodiments, but should be defined only in accordance with the following claims and their equivalents.

What is claimed is:

1. A device for mapping a fluorescence signal from a sample comprising:
    a light source directed at the sample containing a fluorophore which generates the fluorescence signal;
    a pulse generator to produce a light source pulse;
    an active detector with a data acquisition rate between:
        a lower limit of approximately $10^4$ pulses per second (pps); and
        an upper limit of approximately $10^7$ pps, where the active detector has an image acquisition pixel resolution between:
            a lower limit of approximately $10^{-6}$ m×$10^{-6}$ m; and
            an upper limit of approximately $10^{-4}$ m×$10^{-4}$ m;
    a timing circuit to generate a delay between:
        a lower limit of approximately $10^{-12}$ s; and
        an upper limit of approximately $10^{-10}$ s;
    a control circuit to generate a duration;
    a high speed switch controlled by one or both the delay and the duration to selectively direct the fluorescence signal to the active detector, where the fluorescence signal is detected by the active detector after the delay and during the duration; and
    a stepping motor to move the sample position a separation in one or more directions and map the fluorescence signal detected from the sample at different positions.

2. The device of claim 1, where the high speed switch is a Field Effect Transistor switch.

3. The device of claim 1, where the control circuit selects the high speed switching circuit based on a BoxCar Integrator selected.

4. The device of claim 1, where the fluorophore has a half-life of between:
    a lower limit of approximately $10^{-9}$ s; and
    an upper limit of approximately $10^{-8}$ s.

5. The device of claim 1, where the pulse generator is set between:
    a lower limit of approximately $10^4$ pulses per second (pps); and
    an upper limit of approximately $10^7$ pps.

6. The device of claim 1, where the light source is a light emitting diode.

7. The device of claim 1, where the duration of the light source pulse is between:
    a lower limit of approximately $0.5 \times 10^{-9}$ s; and
    an upper limit of approximately $10^{-8}$ s.

8. The device of claim 1, where the separation is between:
    a lower limit of approximately $10^{-6}$ m; and
    an upper limit of approximately $10^{-4}$ m.

9. The device of claim 1, where a response time of the active detector is between:
    a lower limit of approximately $0.5 \times 10^{-9}$ s; and
    an upper limit of approximately $2 \times 10^{-9}$ s.

10. The device of claim 1, where a transit time of the active detector is between:
    a lower limit of approximately $0.5 \times 10^{-9}$ s; and
    an upper limit of approximately $2 \times 10^{-9}$ s.

11. The device of claim 1, where a response time of the active detector to background light is between:
   a lower limit of approximately $0.5 \times 10^{-9}$ s; and
   an upper limit of approximately $2 \times 10^{-9}$ s.

12. The device of claim 1, where an excitation cycle comprises a single light source pulse with a single gate delay and a single detection period, and the control circuit is capable of detecting the fluorescence signal in a single excitation cycle.

13. A method for mapping a fluorophore labeled sample comprising:
   (a) receiving the fluorophore labeled sample with a fluorophore half-life of between:
      a lower limit of approximately $10^{-9}$ s; and
      an upper limit of approximately $4 \times 10^{-9}$ s;
   (b) applying voltages to an active photomultiplier tube;
   (c) orienting the fluorophore labeled sample at an initial x, y location;
   (d) generating a pulse of light from a pulse generator to irradiate the fluorophore labeled sample to generate a fluorescence signal;
   (e) providing a delay generated by a timing circuit;
   (f) providing a duration generated by a control circuit;
   (g) directing the fluorescence signal to the active photomultiplier tube using a switch, where the switch directs the fluorescence signal after the delay and for the duration;
   (h) detecting the fluorescence signal at the initial x, y location with a data acquisition rate and an image acquisition pixel resolution;
   (i) changing the x, y location by a separation;
   (j) repeating steps (d)-(h) until the fluorophore labeled sample has been mapped;
   (k) receiving a duplicate of the fluorophore labeled sample in step (a);
   (l) repeating steps (c)-(j); and
   (m) adding fluorescence detected at each x, y location to map the fluorophore labeled sample.

14. The method of claim 13, where the pulse generator is set between:
   a lower limit of approximately $10^4$ pulses per second (pps); and
   an upper limit of approximately $10^7$ pps.

15. The method of claim 13, where the data acquisition rate is between:
   a lower limit of approximately $10^4$ pulses per second (pps); and
   an upper limit of approximately $10^7$ pps.

16. The method of claim 13, where the image acquisition pixel resolution is between:
   a lower limit of approximately $10^{-6}$ m$\times 10^{-6}$ m; and
   an upper limit of approximately $10^4$ m$\times 10^4$ m.

17. The method of claim 13, where the duration of the pulse of light is between:
   a lower limit of approximately $0.5 \times 10^{-9}$ s; and
   an upper limit of approximately $10^{-8}$ s.

18. The method of claim 13, where the fluorophore labeled sample is moved in discrete steps while being repetitively pulsed in a time interval between each step and the separation is between:
   a lower limit of approximately $10^{-6}$ m; and
   an upper limit of approximately $10^{-4}$ m.

19. A system for mapping a fluorescence signal in a location comprising:
   a light source for generating an emission of light;
   a pulse generator for producing a pulse of the emission of light to excite the fluorescence signal in a fluorophore;
   an active photomultiplier tube;
   a timing circuit to generate a delay between:
      a lower limit of approximately $10^{-12}$ s; and
      an upper limit of approximately $10^{-10}$ s;
   a control circuit to generate a duration;
   a Field Effect Transistor switch to selectively direct a component of the fluorescence signal determined by the delay and the duration to the active photomultiplier tube, where the fluorescence signal is detected by the active photomultiplier tube after the delay and during the duration; and
   a step generator to raster the light source over the location to detect the fluorescence signal at different positions.

\* \* \* \* \*